US010125198B2

(12) United States Patent
Glanville

(10) Patent No.: US 10,125,198 B2
(45) Date of Patent: Nov. 13, 2018

(54) METHOD FOR MASS HUMANIZATION OF NON-HUMAN ANTIBODIES

(71) Applicant: Distributed Bio, Inc., San Francisco, CA (US)

(72) Inventor: Jacob Glanville, San Francisco, CA (US)

(73) Assignee: Distributed Bio, Inc., San Francisco, CA (US)

( * ) Notice: Subject to any disclaimer, the term of this patent is extended or adjusted under 35 U.S.C. 154(b) by 0 days.

(21) Appl. No.: 15/130,843

(22) Filed: Apr. 15, 2016

(65) Prior Publication Data

US 2017/0066844 A1    Mar. 9, 2017

Related U.S. Application Data

(60) Provisional application No. 62/155,421, filed on Apr. 30, 2015, provisional application No. 62/149,440, filed on Apr. 17, 2015.

(51) Int. Cl.
| C07K 16/00 | (2006.01) |
| C07K 16/46 | (2006.01) |
| C40B 30/02 | (2006.01) |
| C40B 50/00 | (2006.01) |
| G06F 19/16 | (2011.01) |

(52) U.S. Cl.
CPC .......... *C07K 16/464* (2013.01); *C07K 16/465* (2013.01); *C40B 30/02* (2013.01); *C40B 50/00* (2013.01); *G06F 19/16* (2013.01); *C07K 2317/24* (2013.01); *C07K 2317/565* (2013.01); *C07K 2317/567* (2013.01)

(58) Field of Classification Search
None
See application file for complete search history.

(56) References Cited

U.S. PATENT DOCUMENTS

| 5,130,238 A | 7/1992 | Malek et al. |
| 5,310,652 A | 5/1994 | Gelfand et al. |
| 5,322,770 A | 6/1994 | Gelfand |
| 5,399,491 A | 3/1995 | Kacian et al. |
| 5,480,784 A | 1/1996 | Kacian et al. |
| 5,527,670 A | 6/1996 | Stanley |
| 5,545,540 A | 8/1996 | Mian |
| 5,854,033 A | 12/1998 | Lizardi |
| 5,939,291 A | 8/1999 | Loewy et al. |
| 6,033,850 A | 3/2000 | Purvis |
| 6,277,605 B1 | 8/2001 | Wijnhoven et al. |
| 6,333,157 B1 | 12/2001 | Miller-Jones et al. |
| 6,410,278 B1 | 6/2002 | Notomi et al. |
| 2004/0058378 A1 | 3/2004 | Kong et al. |
| 2005/0119455 A1* | 6/2005 | Fuh ........................ C07K 16/22 530/328 |
| 2005/0255552 A1 | 11/2005 | Flynn et al. |
| 2008/0227957 A1 | 9/2008 | Leung |
| 2009/0093024 A1* | 4/2009 | Bowers ................ C07K 16/00 435/69.6 |
| 2013/0030157 A1* | 1/2013 | Prassler ............... C07K 16/00 530/387.3 |
| 2013/0165640 A1 | 6/2013 | Escher |
| 2013/0331297 A1* | 12/2013 | Fan ................... C07K 16/3069 506/14 |

FOREIGN PATENT DOCUMENTS

| WO | WO-9118989 A1 | 12/1991 |
| WO | WO-9119818 A1 | 12/1991 |
| WO | WO-9201047 A1 | 1/1992 |
| WO | WO-9206204 A1 | 4/1992 |
| WO | WO-9218619 A1 | 10/1992 |
| WO | WO-9936569 A1 | 7/1999 |
| WO | WO-0049176 A1 | 8/2000 |
| WO | WO-2009155726 A2 | 12/2009 |
| WO | WO-2014124677 A1 | 8/2014 |

OTHER PUBLICATIONS

Rader et al., Proc. Nat. Acad. Sci. USA, 1998, 95: 8910-8915.*
Al-Lazikani, et al., Standard conformations for the canonical structures of immunoglobulins, I997.JMB., 273: 927-948.
Donovan, et al., Genes encoding spore coat polypeptides from Bacillus subtilis, J. Mol. Biol., 1987,196:1-10.
Dunbar, et al., ABangle: characterising the VH-VL orientation, Protein Engineering, Design & Selection, 2013, 26(10): 611-620.
Guatelli, et al., Isothermal, in vitro amplification of nucleic acids by a multienzyme Isothermal, in vitro amplification of nucleic acids by a multienzyme, Biochemistry, Proc. Natl. Acad. Sci. USA, Mar. 1990, 87:1874-78.
Han, et al., Ligand-directed retroviral targeting of human breast cancer cells, Proc. Natl. Acad. Sci. USA , Medical Sciences, Oct. 1995, 92: 9747-51.
Hanes, et al., In vitro selection and evolution of functional proteins by using ribosome display, Proc. Natl. Acad. Sci. USA, Biochemistry, May 1997, 94:4937-4942.
He, et al., Eukaryotic ribosome display with in situ DNA recovery, Nature Methods, 2007, 4(3):281-88.
International search report and written opinion dated Jul. 28, 2016 for PCT Application No. US2016027975.
MacCallum, et al., Antibody-antigen interactions: Contact analysis and binding site topography, J. Mol. Biol., I996, 262:732-745.
EP16780941.7 Extended European Search Report dated Sep. 4, 2018.
Yaghoub et al. humMR1, a highly specific humanized single chain antibody for targeting EGFRvIII. Int Immunopharmac 18(2):304-310 (Feb. 2014). Epub Dec. 25, 2013. DOI: 10.1016/J.INTIMP.2013.12.006.

* cited by examiner

*Primary Examiner* — Hong Sang
(74) *Attorney, Agent, or Firm* — Wilson Sonsini Goodrich & Rosati

(57) ABSTRACT

The present invention relates to a method for producing a population of nucleic acids encoding at least one protein comprising at least one immunoglobulin variable domain having a non-human-derived CDR3 amino acid sequence embedded in essentially human framework sequences, as well as to a population of nucleic acids and a population of proteins relates thereto and uses thereof.

11 Claims, 3 Drawing Sheets

Specification includes a Sequence Listing.

METHOD FOR MASS HUMANIZATION OF NON-HUMAN ANTIBODIES

CROSS-REFERENCE

This application claims the benefit of U.S. Provisional Application No. 62/155,421, filed Apr. 30, 2015 and U.S. Provisional Application No. 62/149,440, filed Apr. 17, 2015 which are hereby incorporated by reference in its entirety.

The instant application contains a Sequence Listing which has been submitted electronically in ASCII format and is hereby incorporated by reference in its entirety. Said ASCII copy, created on Nov. 3, 2017, is named 44561-702_201_SL.txt and is 1,153 bytes in size.

BACKGROUND OF THE INVENTION

Natural immunoglobulins have been used in assays, diagnosis and, to a more limited extent, therapy. However, such uses, especially in therapy, have been hindered by the polyclonal nature of natural immunoglobulins. The advent of monoclonal antibodies of defined specificity increased the opportunities for therapeutic use. However, most monoclonal antibodies are produced following immunization of a rodent host animal with the target protein, and subsequent fusion of a rodent spleen cell producing the antibody of interest with a rodent myeloma cell. They are, therefore, essentially rodent proteins and as such are naturally immunogenic in humans, frequently giving rise to an undesirable immune response termed the HAMA (Human Anti-Mouse Antibody) response.

Previous attempts to decrease the immunogenicity of therapeutic antibodies have traditionally used a human template that is selected by the degree of homology to the donor antibody (the human antibody most homologous to the non-human antibody in the variable region is used as the template for humanization). Although this approach has been shown to work, it limits the possibility of selecting the best human template supporting the donor CDRs. Moreover, a CDR grafted humanized antibody prepared in this way may demonstrate a significantly decreased binding affinity.

SUMMARY OF THE INVENTION

In view of the foregoing, there is a need for methods and libraries which allow for quick and/or effective humanization of antibodies, in particular for mass humanization of antibodies. There is further a need for methods and libraries which allow for identification of humanized antibodies binding to a target of interest in only one selection round and/or without the need for cloning immunoglobulin domains into different vectors during selection. The methods and compositions described herein address these needs, and provided additional advantages as well.

In one aspect, the disclosure provides a method of producing a population of nucleic acids encoding at least one protein comprising at least one immunoglobulin variable domain having a non-human-derived CDR3 amino acid sequence embedded in essentially human framework sequences. In one embodiment, the method comprises the steps of: (a) providing at least one nucleic acid encoding a non-human-derived complementarity determining region 3 (CDR3) amino acid sequence or an amino acid sequence further encompassing 1, 2, or 3 amino acids N-terminal and/or C-terminal of the non-human-derived CDR3 amino acid sequence; (b) generating a population of nucleic acids encoding at least one protein comprising at least one immunoglobulin variable domain having a non-human CDR3 amino acid sequence of step (a) embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a non-human-derived CDR3 amino acid sequence; wherein the nucleic acid sequences encoding the CDR1 and CDR2 amino acid sequences are diversified among the population of nucleic acids encoding at least one protein comprising at least one immunoglobulin variable domain; wherein each nucleic acid sequence encoding a CDR1 or CDR2 amino acid sequence is independently based (i) on a nucleic acid sequence encoding a human CDR1 or CDR2, respectively, or (ii) on a nucleic acid sequence encoding a non-human CDR1 or CDR2, respectively; wherein at least some of the nucleic acid sequences encoding a CDR1 or CDR2 amino acid sequence have been modified to encode at least one amino acid present in non-human CDR1 or CDR2 amino acid sequences, respectively, in case of human CDR1 or CDR2, respectively, or to encode at least one amino acid present in human CDR1 or CDR2 amino acid sequences, respectively, in case of non-human CDR1 or CDR2, respectively; and wherein the human FR1, FR2, FR3 and FR4 regions are human framework regions selected to provide a scaffold conducive for non-human CDR3 amino acid sequences, with the proviso: that the two C-terminal amino acids of FR2 are optionally non-human, and that the two C-terminal amino acids of FR3 are optionally non-human.

In another aspect, the disclosure provides a method of producing a population of nucleic acid sequences encoding at least one protein comprising at least one immunoglobulin variable domain having a non-human-derived CDR3 amino acid sequence embedded in essentially human framework sequences. In some embodiments, the method comprises one or more steps of a process as described herein.

In another aspect, the disclosure provides a method of producing a population of amino acid sequences for one or more proteins comprising at least one immunoglobulin variable domain having a non-human-derived CDR3 amino acid sequence embedded in essentially human framework sequences. In some embodiments, the method comprises one or more steps of a process as described herein.

In one aspect, the disclosure provides a population of nucleic acids in accordance with any of the methods described herein.

In one aspect, the disclosure provides a population of proteins in accordance with any of the methods described herein.

In one aspect, the disclosure provides a system for performing any of the methods described herein. In some embodiments, the system comprises a computer processor programmed to perform one or more steps of the method.

In one aspect, the disclosure provides computer readable medium comprising machine executable code that upon execution by one or more computer processors implements any of the methods described herein.

In one aspect, the disclosure provides uses of the various compositions described herein with regard to any of the various aspects. In some embodiments, a composition of the disclosure is used in the preparation of a medicament for the treatment of a disease or condition of a subject.

In one aspect, the disclosure provides a method of treating a subject for a disease or condition. In some embodiments, the method comprises administering to a subject one or more proteins of any of the various aspects disclosed herein.

INCORPORATION BY REFERENCE

This application claims the benefit of and priority to provisional U.S. patent application Ser. No. 62/155,421, filed on Apr. 30, 2015, and provisional U.S. patent application Ser. No. 62/149,440, filed on Apr. 17, 2015, both of which are incorporated herein by reference. All publications, patents, and patent applications mentioned in this specification, and applications to which the present application claims the benefit of priority are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
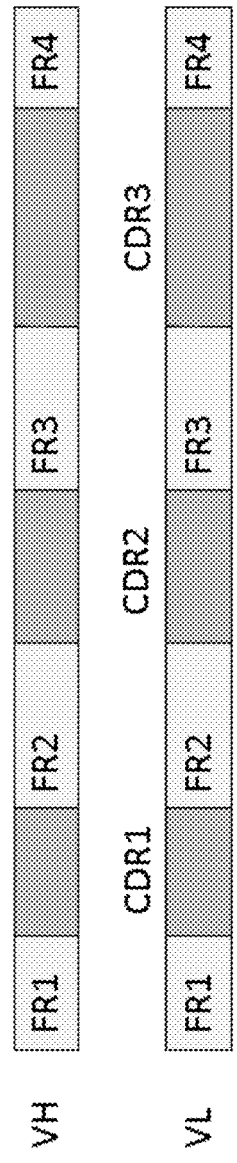
FIG. 1 shows the structure of light and heavy chain immunoglobulin framework regions and CDRs.
Figure 2:
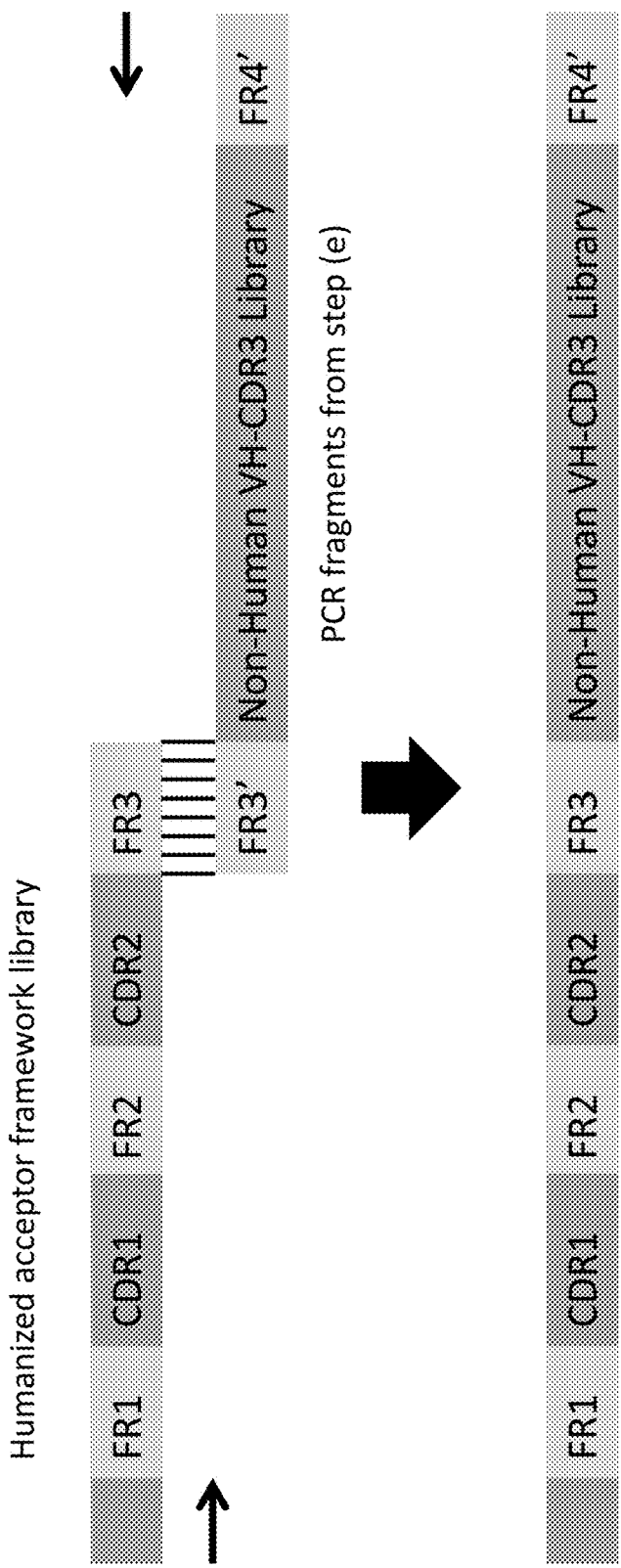
FIG. 2 shows how overlap PCR can be used to generate humanized acceptor libraries containing non-human CDR3 sequences.

Throughout this application, various embodiments may be presented in a range format. It should be understood that the description in range format is merely for convenience and brevity and should not be construed as an inflexible limitation. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The systems and methods of this disclosure as described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, et al., Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Stryer, L., Biochemistry (4th Ed.) W.H. Freeman, N.Y. (1995); Gait, "Oligonucleotide Synthesis: A Practical Approach" IRL Press, London (1984); Nelson and Cox, Lehninger, Principles of Biochemistry, 3rd Ed., W.H. Freeman Pub., New York (2000); and Berg et al., Biochemistry, 5th Ed., W.H. Freeman Pub., New York (2002), all of which are herein incorporated by reference in their entirety for all purposes. Before the present compositions, research tools and systems and methods are described, it is to be understood that this disclosure is not limited to the specific systems and methods, compositions, targets and uses described, as such may, of course, vary. It is also to be understood that the terminology used herein is for the purpose of describing particular aspects only and is not intended to limit the scope of the present disclosure, which will be limited only by appended claims.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

Native antibodies and immunoglobulins are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of the beta-sheet structure. The CDRs in each chain are held together in close proximity by the FR regions and, with the CDRs from the other chain, contribute to the formation of the antigen-binding site of antibodies (see e.g. Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known. The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

CDR-1H, CDR-2H, and CDR-3H denote immunoglobulin heavy chain complementarity determining region 1, 2 and 3 respectively. VHFR1, VHFR2, and VHFR3 VHFR4 denote immunoglobulin heavy chain framework region 1, 2, 3 and 4 respectively. CDR-1L, CDR-2L, and CDR-3L denote immunoglobulin light chain complementarity determining region 1, 2 and 3 respectively. VLFR1, VLFR2, and VLFR3 VLFR4 denote immunoglobulin light chain framework region 1, 2, 3 and 4 respectively.

The heavy/light (H/L) interface mount angle is measured as the degree shift of the central axis of the light chain Fv compared to a fixed superposition of heavy chain Fv in a predicted or observed crystal structures. Non-limiting exemplary methods of determining the H/L interface mount angle, alternately referred to as the packing angle, can be found in Dunbar et al. ABangle: characterizing the VH-VL orientation in antibodies. Protein Engineering, Design, and Selection 26, 611-620 (2013).

A positional weight matrix can be a matrix indicating, for each of a plurality of positions within a polypeptide, the relative frequency of a given amino acid within a population of variants of the polypeptide. For example, if a multiple protein alignment indicates that three variants have an S, R, and a T at a given position in an alignment, then within the positional weight matrix at that position would be [S:0.33, R:0.33, T:0.33] indicating the identity and relative frequency of the amino acid.

In one aspect, the disclosure provides a method for producing a population of nucleic acids encoding at least one protein comprising at least one immunoglobulin variable domain having a non-human-derived CDR3 amino acid sequence embedded in essentially human framework sequences, as well as to a population of nucleic acids and a population of proteins relates thereto and uses thereof.

In one aspect, provided herein is a method for producing a population of nucleic acids encoding at least one protein comprising at least one immunoglobulin variable domain having a non-human-derived CDR3 amino acid sequence embedded in essentially human framework sequences. The method can comprise the following steps: (a) providing at least one nucleic acid encoding a non-human-derived complementarity determining region 3 (CDR3) amino acid sequence or an amino acid sequence further encompassing 1, 2, or 3 amino acids N-terminal and/or C-terminal of the non-human-derived CDR3 amino acid sequence and (b) generating a population of nucleic acids encoding at least one protein comprising at least one immunoglobulin variable domain having a non-human CDR3 amino acid sequence of step (a) embedded in essentially human framework sequences. The human framework sequences can comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a non-human-derived CDR3 amino acid sequence. The nucleic acid sequences encoding the CDR1 and CDR2 amino acid sequences can be diversified among the population of nucleic acids encoding at least one protein comprising at least one immunoglobulin variable domain, wherein each nucleic acid sequence encoding a CDR1 or CDR2 amino acid sequence is independently based (i) on a nucleic acid sequence encoding a human CDR1 or CDR2, respectively, or (ii) on a nucleic acid sequence encoding a non-human CDR1 or CDR2, respectively, wherein at least some of the nucleic acid sequences encoding a CDR1 or CDR2 amino acid sequence have been modified to encode at least one amino acid present in non-human species CDR1 or CDR2 amino acid sequences, respectively, in case of human CDR1 or CDR2, respectively, or to encode at least one amino acid present in human CDR1 or CDR2 amino acid sequences, respectively, in case of non-human species CDR1 or CDR2, respectively. The human FR1, FR2, FR3 and FR4 regions can be human framework regions selected to provide a scaffold conducive for non-human CDR3 amino acid sequences, with the proviso that the two C-terminal amino acids of FR2 are optionally non-human, and that the two C-terminal amino acids of FR3 are optionally non-human.

Non-limiting examples of non-human species contemplated herein include mouse, dog, cats, zebrafish, llamas, shark, cow, and rats. In one instance a non-human species can be selected from the group consisting of mouse, rat, dog, cat, cow, sheep, pig, horse, donkey, goat, chicken, ferret, pika, bat, llama, bear, tiger, wolf, fox, lion, cheetah, giraffe, African wild dog, monkey, ape, orangutan, chimpanzee, rhesus monkey, macaque, squirrel, lizard, snake, alligator, turtle, crocodile, tortoise, toad, frog, newt, salamander, duck, goose, guinea fowl, guinea pig, hamster, penguin, ostrich, quail, turkey, owl, scrub jay, zebrafish, catfish, eel, shark, swordfish, Antarctic fish (TrBel), Antarctic fish (GyAcl), white sturgeon, or any other animal that produces immunoglobulins.

"A population of nucleic acids" is understood as 2 or more nucleic acids, preferably 2, 3, 4, 5, 6, 7, 8, 9, 10, 50, 100, 150, 200 or more nucleic acids, wherein at least 2 of the nucleic acids of the population exhibit different nucleic sequences, more preferably wherein at least 2, 3, 4, 5, 6, 7, 8, 9, 10, 50, 100, 150, 200 or more nucleic acids of the population exhibit different nucleic sequences, and/or wherein at least 50%, at least 80%, at least 90%, at least 95%, at least 96%, at least 97%, at least 98%, at least 99% or 100% of the nucleic acids of the population exhibit different nucleic sequences.

In some embodiments, an encoded protein comprises at least one immunoglobulin variable domain, preferably 1, 2, 3, 4 or more immunoglobulin variable domains, more preferably 1 or 2 immunoglobulin variable domains. For example, a variable heavy immunoglobulin domain may be paired with a variable light domain to provide an antigen binding site; such as in an scFv. Alternatively, independent regions, e.g., a variable heavy domain alone or a variable light domain alone may be used. An immunoglobulin variable domain comprises CDR1, CDR2 and CDR3 sequences. In particular, an immunoglobulin variable heavy domain comprises CDR-1H, CDR-2H and CDR-3H sequences, and an immunoglobulin variable light domain comprises CDR-1L, CDR-2L and CDR-3L sequences.

A "non-human CDR3 amino acid sequence" is understood as an amino acid sequence which is identical to a CDR3 amino sequence naturally occurring in a non-human antibody. The CDR3 amino sequence may be a CDR-3L or a CDR-3H amino acid sequence.

A "non-human-derived CDR3 amino acid sequence" is understood as an amino acid sequence which is identical to a CDR3 amino sequence naturally occurring in a non-human antibody, or which contains 1, 2, 3, 4, or 5 amino acid mutations compared to a CDR3 amino sequence naturally occurring in a non-human antibody, preferably wherein the mutation is a conservative mutation.

Conservative amino acid substitutions, as one of ordinary skill in the art will appreciate, are substitutions that replace an amino acid residue with one imparting similar or better (for the intended purpose) functional and/or chemical characteristics. For example, conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis. The altered polypeptides are then tested for retained or better function using functional assays available in the art.

Nucleic acid molecules may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

The nucleic acids may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

The term "embedded in essentially human framework sequences" is understood as that the CDR3-derived sequence is located within the framework sequences to yield an immunoglobulin variable domain. For example, a skilled person is aware that a CDR-3L amino acid sequence is located between FR3 and FR4 framework regions of the light chain in case of an immunoglobulin light chain variable domain.

"Human framework sequences" are understood as framework sequences which are naturally occurring human framework sequences. The nucleic acids encoding the human framework sequences may contain silent mutations as compared to the naturally occurring nucleic acids encoding the human framework sequences and/or sequences that are a result of the degeneration of the genetic code. There are 20 natural amino acids, most of which are specified by more than one codon. Therefore, all nucleotide sequences are included which result in the human framework sequences as defined above.

An "essentially human framework sequence" is understood as framework sequence which exhibits at least 90%, preferably at least 95%, 96%, 97%, 98%, or 99% sequence identity to a naturally occurring human framework sequence. In a preferred embodiment, the essentially human framework sequence consists of FR1, FR2, FR3 and FR4 regions, which are human FR1, FR2, FR3 and FR4 regions, with the proviso that the two C-terminal amino acids of FR2 are optionally non-human, and that the two C-terminal amino acids of FR3 are optionally non-human, more preferably, the two C-terminal amino acids of heavy FR2 are optionally non-human, and that the two C-terminal amino acids of heavy FR3 are optionally non-human.

"An amino acid sequence further encompassing 1, 2, or 3 amino acids N-terminal and/or C-terminal of the non-human-derived CDR3 amino acid sequence" is understood as that the non-human-derived CDR3 amino acid sequence further comprises 1, 2, or 3 amino acids N-terminal of the non-human-derived CDR3 amino acid sequence, and/or 1, 2, or 3 amino acids C-terminal of the non-human-derived CDR3 amino acid sequence.

A "non-human-derived amino acid sequence" is understood as an amino acid sequence which is identical to a amino sequence naturally according in a non-human antibody, or which contains 1, 2, 3, 4, or 5 amino acid mutations compared to an amino sequence naturally occurring in a non-human species antibody, preferably wherein the mutation is a conservative mutation.

In some embodiments, at least one nucleic acid encoding a non-human-derived complementarity determining region 3 (CDR3) amino acid sequence or an amino acid sequence further encompassing 1, 2, or 3 amino acids N-terminal and/or C-terminal of the non-human species-derived CDR3 amino acid sequence is provided. In a preferred embodiment, 1, 2, 3, 4, 5, 6, 7, 8, 9, 10, 15, 20, 50, 100 or more nucleic acids as defined above are provided. In general, the methods and populations of the disclosure are suitable for mass hybridization of the non-human antibodies, and for providing a mass humanized library suitable for this purpose. Therefore, it is preferred that more than one, preferably 2, 3, 4, 5, 6, 7, 8, 9, 10, 15, 20, 50, 100 or more nucleic acids as defined above are provided.

For efficient mass hybridization, it is preferred that the same method is used for transferring the non-human or non-human-derived CDR3 regions into an Acceptor Framework of the disclosure, to obtain the population of nucleic acids of step (b), which preferably represents nucleic acids encoding a humanized library of antibodies. Therefore, it is preferred to provide either always CDR3 regions of the non-human antibodies, or always a CDR3 region which further encompasses 1, 2, or 3 amino acids N-terminal and/or C-terminal of the non-human-derived CDR3 amino acid sequence.

Therefore, in a further preferred embodiment, more than one, preferably 2, 3, 4, 5, 6, 7, 8, 9, 10, 15, 20, 50, 100 or more nucleic acids as defined above are provided, wherein the each nucleic acid encodes a non-human-derived complementarity determining region 3 (CDR3) amino acid sequence, preferably a mouse complementarity determining region 3 (CDR3) amino acid sequence.

In a yet further preferred embodiment, more than one, preferably 2, 3, 4, 5, 6, 7, 8, 9, 10, 15, 20, 50, 100 or more nucleic acids as defined above are provided, wherein the each nucleic acid encodes a non-human-derived complementarity determining region 3 (CDR3) amino acid sequence, preferably a non-human complementarity determining region 3 (CDR3) amino acid sequence, which further encompasses 1, 2, or 3 amino acids N-terminal and/or C-terminal of the non-human-derived CDR3 amino acid sequence.

The phrase "interspaced by" in the context of the methods of the disclosure is understood that two amino acid sequences are connected via the interspacing amino acid sequence, preferably by peptide linkages. For example, a protein comprising the structure FR1-CDR1-FR2 is understood as that FR1 and FR2 regions are interspaced by a CDR1.

"CDR1 and CDR2 amino acid sequences are diversified among the population" is understood as that at least 2 of the nucleic acids of the population exhibit different CDR1 nucleic sequences, in particular different CDR-1H and/or CDR-1L sequences, and/or at least 2 of the nucleic acids of the population exhibit different CDR2 nucleic sequences, in particular different CDR-2H and/or CDR-2L sequences, more preferably wherein at least 2, 3, 4, 5, 6, 7, 8, 9, 10, 50, 100, 150, 200 or more nucleic acids of the population exhibit different CDR1 and/or CDR2 nucleic sequences, and/or wherein at least 50%, at least 80%, at least 90%, at least 95%, at least 96%, at least 97%, at least 98%, at least 99% or 100% of the nucleic acids of the population exhibit different CDR1 and/or CDR2 nucleic sequences.

In some embodiments, each nucleic acid sequence encoding a CDR1 or CDR2 amino acid sequence is independently based (i) on a nucleic acid sequence encoding a human CDR1 or CDR2, respectively, or (ii) on a nucleic acid sequence encoding a non-human (e.g., mouse) CDR1 or CDR2, respectively. "Based on" is understood as that, in case of a CDR1 sequence, the CDR1 amino acid sequence contains at least 3, 4, 5, 6, 7, 8, 9 or more, for example all, amino acids of a human CDR1, in the case of (i), or of a non-human CDR1, in case of (ii), respectively, and/or exhibits at least 30%, at least 50%, at least 80%, at least 90%, at least 95%, or 100% sequences identity to a human CDR1 (in case of i) or to a non-human CDR1 (in case of ii), respectively.

It is understood that the sequence comparison apply to the respective CDR1 regions; e.g. a CDR-1H region based on a human CDR-1H is compared to human CDR-1H regions.

A "scaffold conducive for non-human CDR3 amino acid sequences" is understood as a immunoglobulin scaffold which is suitable for a successful graft of a non-human CDR3 amino acid sequence to yield a correctly folded antibody for at least 30%, at least 50%, or at least 60%, 70% or 80% of grafted non-human CDR3 amino acid sequences, and/or which exhibits at least 30%, at least 50%, at least 80%, or at least 90%, framework homology to a non-human framework, and/or which exhibits CDR cosmology, and/or wherein the CDR sequences exhibit canonical structures, and/or wherein the grafted non-human CDR3 sequences can adopt comfortable heavy or light mount angles, respectively. The rationale is that the framework scaffold serves to hold the non-human-derived CDR3 sequences in their correct spatial orientation for interaction with an antigen. Thus, if the selected essentially human framework sequences selected to be similar to the non-human frameworks, it will maximize the likelihood that affinity will be retained in the mass humanized antibodies.

Determining CDR regions and framework regions can be performed by methods known in the art, as for example described in the chapter Protein Sequence and Structure Analysis of Antibody Variable Domains (in: Antibody Engineering Lab Manual, 2001 (Ed.: Duebel, S. and Kontermann, R., Springer-Verlag, Heidelberg).

For example, the CDR regions can be determined using the Kabat nomenclature, as described in Kabat et al. (Sequences of Proteins of Immunological Interest, 5th Ed. Public Health Service, National Institutes of Health, Bethesda, Md. (1991)), the Chothia nomenclature, as for example described in Al-Lazikani et al., ((1997) JMB 273, 927-948), the Martin nomenclature or the Contact nomenclature, as described in MacCallum, R. M., Martin, A. C. R. and Thornton, J. T. (1996; Antibody-antigen interactions: Contact analysis and binding site topography. J. Mol. Biol. 262, 732-745).

TABLE 1

An overview on the location of a CDR region.

| Loop | Kabat | Chothia | Contact |
|------|-------|---------|---------|
| L1 | L24 - - - L34 | L24 - - - L34 | L30 - - - L36 |
| L2 | L50 - - - L56 | L50 - - - L56 | L46 - - - L55 |
| L3 | L89 - - - L97 | L89 - - - L97 | L89 - - - L96 |
| H1 | H31 - - - H35B (Kabat Numbering) | H26 - - - H32 . . . 34 | H30 - - - H35B |
| H1 | H31 - - - H35 (Chothia Numbering) | H26 - - - H32 | H30 - - - H35 |
| H2 | H50 - - - H65 | H52 - - - H56 | H47 - - - H58 |
| H3 | H95 - - - H102 | H95 - - - H102 | H93 - - - H101 |

In a preferred embodiment, the Kabat nomenclature is applied.

CDR-H3 has a length of 3 to 25 amino acids, and preferably starts 33 residues after the end of CDR-H2 and generally 2 after a Cys. Residues before CDR-H3 are preferably Cys-XXX-XXX, and are typically Cys-Ala-Arg. Residues after CDR-H3 are preferably Trp-Gly-XXX-Gly.

By the populations and methods of the disclosure, general solutions to a non-human antibody repertoire is provided, instead of providing single solutions to a single antibody example, thereby allowing mass humanization of a set of non-human antibodies and providing humanized antibodies binding to a target of interest specifically and/or with high affinity, even after a single selection round.

The human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. The FR1 and FR4 regions can be human FR1 and FR4 regions. As also described above, it is possible that a nucleic acid encoding a non-human-derived CDR3 amino acid sequence, preferably a non-human-CDR3 amino acid sequence, further comprising 1, 2, or 3 amino acids N-terminal of the non-human-derived CDR3 amino acid sequence, and/or 1, 2, or 3 amino acids C-terminal of the non-human-derived CDR3 amino acid sequence is provided, in particular in case a nucleic acid encoding a non-human specificity determining region (SDR) as described above is provided. For example an SDR comprising the CDR-3H may be grafted.

Further, FR2 is a human FR2 framework region, or the two C-terminal amino acids of FR2 are optionally non-human.

In one preferred embodiment, FR2 is a human FR2 framework region.

Various methods are available for providing a population of nucleic acids according to step (b) of the above method, starting from the at least one nucleic acids of step (a).

For example, it is possible to generate a set of oligonucleotides comprising sequences encoding non-human CDR3 regions and add those via PCR to pre-amplified VH and VL libraries with the features of the disclosure.

This can be followed by a PCR to assemble the VH and VL sequences into a suitable antibody format for display, such as an scFv. Subsequently, the construct can be ligated into a suitable display vector, such as a phagemid vector.

In some embodiments, the nucleic acids of step (a), "providing at least one nucleic acid encoding a non-human-derived complementarity determining region 3 (CDR3) amino acid sequence or an amino acid sequence further encompassing 1, 2, or 3 amino acids N-terminal and/or C-terminal of the non-human-derived CDR3 amino acid sequence," are provided by: (1) determining the nucleic acid sequence(s) of at least one CDR3 region, preferably CDR-3H and CDR-3L region, of at least one non-human antibody, or of a region further comprising 1, 2, or 3 amino acids N-terminal of the non-human CDR3 amino acid sequence; (2) providing at least one oligonucleotide, which has the following structure: FR3'-CDR3-FR4', wherein FR3' represents a sequence encoding a human FR3 region, or a fragment thereof comprising the C-terminal end of the FR3 region, and wherein FR4' represents a sequence encoding a human FR4 region, or a fragment thereof comprising the N-terminal end of the FR4 region; (3) generating the population of nucleic acids of (b) by PCR, in particular encompassing overlap PCR.

Determining the nucleic acid sequence of a CDR3 region of gene encoding an antibody can be performed by sequencing methods known in the art.

An oligonucleotide can be produced by methods known in the art, such as solid phase synthesis.

In a preferred embodiment, the population of nucleic acids encodes proteins comprising at least a VH domain and at least one VL domain, more preferably the nucleic acids encode an scFv.

In a preferred embodiment, step (3) comprises: generating a population of nucleic acids encoding at least one variable domain by PCR using a population of template nucleic acids, wherein the template nucleic acids comprise Acceptor Framework nucleic acids of the disclosure.

Thereby, a library comprising a VH domain, or a VL domain, respectively, is generated.

In a further preferred, a population of nucleic acids encoding a protein comprising a VH domain and a VL domain, in particular an scFv, according to the disclosure is generated.

Therefore, in a more preferred embodiment, step (3) above further comprises generating nucleic acids encoding a protein comprising a VH domain and a VL domain, in particular an scFv, by overlap PCR.

It is understood that FR3 and FR4 are heavy chain FR3 and FR4 in case of CDR-3H, and that FR3 and FR4 are light chain FR3 and FR4 in case of CDR-3L.

In a preferred embodiment, the nucleic acid sequence moieties FR3' and FR4', respectively, both independently have a length which allows for stable base pairing with the corresponding complementary strand under suitable conditions. In particular, the length of FR3' and FR4' independently is at least about 15 nucleotides, preferably at least about 15, 16, 17, 18, 19, 20, 21, 22, 23, 24, 25, 26, 27, 28, 29, 30, 31, 32, 33, 43, 35 or more nucleotides. For example, the length is up to 50, 75 or 100 nucleotides. For example, FR3' may be a nucleic acid encoding human FR3. For example, FR4' may be a nucleic acid encoding human FR4.

Therefore, in a preferred embodiment, step (a) of the above method comprises: generating a population of nucleic acids comprising: (i) a sequence encoding a human FR3 region, or a fragment thereof comprising the C-terminal end of the FR3 region; (ii) a sequence encoding a non-human-derived CDR3 amino acid sequence or an amino acid sequence further encompassing 1, 2, or 3 amino acids N-terminal and/or C-terminal of the non-human-derived CDR3 amino acid sequence; and (iii) a sequence encoding a human FR4 region, or a fragment thereof comprising the N-terminal end of the FR4 region, with the proviso that the two C-terminal amino acids of FR3 are optionally non-human.

Alternatively, Acceptor Framework nucleic acid sequence may be provided, which comprise FR1, FR2, FR3 and FR4 regions, and CDR1 and CDR2 regions of the disclosure, respectively. Non-human-derived CDR3 regions may be cloned into the Acceptor Framework nucleic acids by suitable methods. Therefore, in a further preferred embodiment, step (b) of the above method comprises: (i)

providing a population of Acceptor Framework nucleic acid sequences, wherein each Acceptor Framework nucleic acid sequence comprises nucleic acid sequences encoding a set of framework regions comprising a first human framework region (FR1), a second human framework region (FR2), a third human framework region (FR3), and a fourth human framework region (FR4), wherein the FR1 and FR2 regions are interspaced by a complementarity determining region 1 (CDR1), the FR2 and FR3 regions are interspaced by a complementarity determining region 2 (CDR2), and the nucleic acid sequences encoding FR3 and FR4 regions are linked directly or are interspaced by a stuffer nucleic acid sequence, and (ii) combining at least one nucleic acid sequence encoding a non-human-derived CDR3 amino acid sequence with an Acceptor Framework nucleic acid sequence, so that the FR3 and FR4 regions are interspaced by a non-human-derived CDR3 amino acid sequence or an amino acid sequence further encompassing 1, 2, or 3 amino acids N-terminal and/or C-terminal of the non-human-derived CDR3 amino acid sequence, with the proviso that the two C-terminal amino acids of FR2 are optionally non-human, and that the two C-terminal amino acids of FR3 are optionally non-human.

An "Acceptor Framework nucleic acid" according to the present disclosure refers to a nucleic acid sequence that comprises the nucleic acid sequences encoding the FR1, FR2, FR3 and FR4 regions, and the nucleic acid sequences encoding a CDR1 and a CDR2 region or amino acid sequences that can fulfill the role of these CDRs, as defined herein, with the structure FR1-CDR1-FR2-CDR2-FR3-L-FR4, wherein L is either a direct linkage or a stuffer nucleic acid sequence, which direct linkage or stuffer nucleic acid sequence serves as the site of integration for a nucleic acid encoding a non-human-derived CDR3 amino acid sequence, preferably a non-human-CDR3 amino acid sequence, or a non-human-derived CDR3 amino acid sequence, preferably a non-human-CDR3 amino acid sequence further comprising 1, 2, or 3 amino acids N-terminal of the non-human-derived CDR3 amino acid sequence, and/or 1, 2, or 3 amino acids C-terminal of the non-human-derived CDR3 amino acid sequence.

Accordingly, an "Acceptor Framework" according to the present disclosure refers to a protein comprising the FR1, FR2, FR3 and FR4 regions, and the CDR1 and CDR2 regions, or amino acid sequences that can fulfill the role of these CDRs, as defined herein, with the structure FR1-CDR1-FR2-CDR2-FR3-L-FR4, wherein L is either a direct peptide linkage or a stuffer sequence, wherein the corresponding nucleic acid direct linkage or stuffer nucleic acid sequence serves as the site of integration for a nucleic acid encoding a non-human-derived CDR3 amino acid sequence, preferably a non-human-CDR3 amino acid sequence, or a non-human-derived CDR3 amino acid sequence, preferably a non-human-CDR3 amino acid sequence further comprising 1, 2, or 3 amino acids N-terminal of the non-human-derived CDR3 amino acid sequence, and/or 1, 2, or 3 amino acids C-terminal of the non-human-derived CDR3 amino acid sequence. The Acceptor Framework can be a variable heavy chain (VH) Acceptor Framework or a variable light chain (VL) Acceptor Framework, or can be a Framework comprising a variable heavy chain (VH) Acceptor Framework and a variable light chain (VL) Acceptor Framework, such as an scFv Acceptor Framework comprising insertion sites for CDR-3H and CDR-3L.

In a further preferred embodiment, the nucleic acid sequences encoding the non-human-derived CDR3 amino acid sequences or the amino acid sequence further encompassing 1, 2, or 3 amino acids N-terminal and/or C-terminal of the non-human-derived CDR3 amino acid sequence are diversified among the population of nucleic acids encoding at least one protein comprising at least one immunoglobulin variable domain.

"The nucleic acid sequences encoding the non-human-derived CDR3 amino acid sequences or the amino acid sequence further encompassing 1, 2, or 3 amino acids N-terminal and/or C-terminal of the non-human-derived CDR3 amino acid sequence are diversified among the population of nucleic acids" is understood as that at least 2 of the nucleic acids of the population encode different CDR3 amino acid sequences, in particular different CDR-3H and/or CDR-3L amino acid sequences, more preferably wherein at least 2, 3, 4, 5, 6, 7, 8, 9, 10, 50, 100, 150, 200 or more encode different CDR3 amino acid sequences, in particular different CDR-3H and/or CDR-3L amino acid sequence, and/or wherein at least 50%, at least 80%, at least 90%, at least 95%, at least 96%, at least 97%, at least 98%, at least 99% or 100% of the nucleic acids of the population encode different CDR3 amino acid sequences, in particular different CDR-3H and/or CDR-3L amino acid sequences. In a more preferred embodiment the, sequences are diversified due to immunization of one or more non-humans with a target of interest. Preferably, the sequences are diversified within the CDR3 amino acid sequence, in case the sequence further encompasses 1, 2, or 3 amino acids N-terminal and/or C-terminal of the non-human-derived CDR3 amino acid sequence.

It is preferred to use the sequences identical to the CDR3 regions of non-human antibodies raised against the antigen of interest. As described above, the nucleic acids encoding a non-human CDR3 region can be obtained such as by amplification (e.g. by PCR methods), or by chemical synthesis. Alternatively, an SDR region may be cloned. Such SDR region encompasses 3 further amino acids N-terminal and 1 amino acid C-terminal of CDR3 in case of CDR-3H, as shown above. By using the non-human CDR3 regions or a sequence further encompassing 1, 2, or 3 amino acids N-terminal and 1 amino acid C-terminal of the non-human CDR3 amino acid sequence, efficient mass humanization of the non-human antibodies can be achieved, with a high likelihood of obtaining a successful antibody graft for the CDR3. An SDR is known as a CDR plus an additional few additional boundary residues known in art as "vernier zones".

In a further preferred embodiment, a nucleic acid sequence encoding a non-human-derived CDR3 amino acid sequence is a nucleic acid sequence encoding a non-human CDR3 amino acid sequence, or an amino acid sequence further encompassing 1, 2, or 3 amino acids N-terminal and 1 amino acid C-terminal of the non-human CDR3 amino acid sequence.

In a preferred embodiment, the CDR3 amino acid sequence is a non-human CDR3 amino acid sequence. Such non-human sequences are naturally occurring in the non-human. Antibodies are preferably antibodies produced by B cells, in particular after immunization of the non-human with an antigen of interest. Suitable immunization protocols and protocols for isolating sources of B cells are known in the art, such as bone marrow cells, PBMC cells or spleen cells. Therefore, in an even more preferred embodiment, the non-human CDR3 amino acid sequence, or an amino acid sequence further encompassing 1, 2, or 3 amino acids N-terminal and 1 amino acid C-terminal of the non-human CDR3 amino acid sequence is obtained from a non-human bone marrow cell, PBMC cell or spleen cell, more preferably wherein the non-human was immunized against an antigen of interest.

In a preferred embodiment, it is possible to use a plurality or all of the non-human CDR3 sequences determined in one or more non-humans immunized with an antigen of interest.

In further preferred embodiments, a preselection of non-human CDR3 sequences is performed in step (a). Such preselection can be performed as follows: (i) RNA or DNA is extracted from a B cell source of at least one non-human immunized against an antigen of interest, such as non-human spleen, bone marrow, blood, or the lymph node; (ii) nucleic acids encoding the protein sequence comprising the CDR-3H and optionally CDR-3L regions of the antibody repertoire of the non-humans are amplified; in particular the VH and VL Fav fragment, or minimally the CDR-3H and optionally CDR-3L sequences are amplified; (iii) the amplified products are sequenced; (iv) the resulting sequences are analyzed to identify the translated or untranslated CDR-3H and optionally CDR-3L sequences; (v) the frequency of the CDR-3H and optionally CDR-3L sequences, respectively, of the analyzed repertoire is analyzed, and trees of related CDR-3H and optionally CDR-3L sequences, respectively, are generated by single linkage; (vi) optionally, CDR-3H and optionally CDR-3L sequences which are also determined in a sample obtained from the at least one non-human prior to immunization are excluded; (vii) candidate lineages are ranked by expansion, isotope, somatic hypermutation, tree complexity, and convergence; (viii) individual representatives of each lineage are selected and synthesized, wherein silent or non-silent mutations or natural degeneracy can be incorporated during synthesis; (viii) generating a nucleic acid population of the disclosure comprising the non-human CDR3 regions, e.g. by methods described above.

Therefore, in a particularly preferred embodiment, the non-human CDR3 amino acid sequence, or an amino acid sequence further encompassing 1, 2, or 3 amino acids N-terminal and 1 amino acid C-terminal of the non-human CDR3 amino acid sequence is obtained by: (i) determining the sequence of the non-human CDR3 regions of the antibodies in a sample obtained from a non-human immunized against an antigen of interest; (ii) determining the frequency of all non-human CDR3 amino acid sequence in the sample and generating lineage trees; (iii) optionally excluding non-human CDR3 amino acid sequence sequences present in a sample from the non-human prior to immunization; (iv) ranking candidate lineages by expansion, isotope, somatic hypermutation, tree complexity, and/or convergence; (v) selecting an individual non-human CDR3 amino acid sequence representative of at least one lineage, in particular of a plurality of lineages or all lineages; and (vi) generating a nucleic acid encoding a peptide comprising the individual non-human CDR3 amino acid sequence, or a derivative thereof containing 1, 2 or 3 conservative amino acid mutations.

As described above, it is possible that the two C-terminal amino acids of the FR3, in particular of heavy FR3 are non-human, in particular in case an SDR encompassing a non-human CDR-3H is amplified and grafted to obtain the nucleic acids of the population of the disclosure. As also described above, it is possible that two C-terminal amino acids of the FR2 region are non-human.

It is, however, also possible to incorporate sequences encoding peptide consisting of a non-human-derived complementarity determining region 3 (CDR3) amino acid sequence. In this embodiment, it is preferred that the FR3 region, in particular the heavy FR3 region and the light FR3 region is human. Further, it is possible to use a human FR2 region. Therefore, in another preferred embodiment, the FR2 region is human, and/or the FR3 region is human.

The methods herein encompass in one preferred embodiment the following steps:

Step 1: Cloning of Non-human VH-CDR3 regions between Human VH-FR3 and Human VH-FR4 regions in an acceptor vector Step 2: Transformation of E. coli with the ligation from step 1 to generate a Non-human VH-CDR3 library between Human VH-FR3 and Human VH-FR4 regions Step 3: PCR amplification using DNA template from transformed bacteria from step 2 of Non-human VH-CDR3 library between Human VH-FR3 and Human VH-FR4 regions Step 4: Assembly of Non-human VL-CDR3 regions into an acceptor vector containing synthesized human FR1, FR2 and FR3 domains and a library of CDR1 and CDR2 sequences Step 5: Transformation of E. coli with the ligation from step 4 to generate a Non-human VL-CDR3 library between Human VL-FR3 and Human VL-FR4 regions Step 6: PCR amplification using a synthesized DNA template containing Human FR1, FR2 and FR3 domains and a library of VH-CDR1 and VH-CDR2

Step 7: Assembly of a VH variable region library containing Human Framework regions FR1, FR2 and FR3 separated by a library of CDR1 and CDR2 sequences and a library of Non-human CDR3 sequences via overlap PCR Step 8: PCR of the VH variable region library from step 7 containing Human Framework regions FR1, FR2, FR3 and FR4 separated by a library of CDR1, CDR2 and a library of Non-human CDR3 sequences Step 9: PCR amplification of a VL variable region library containing the C-terminal part of a Human VH-FR4 domain, a linker sequence, Human VL Framework domain regions FR1, FR2, FR3 and FR4 separated by a library of CDR1 and CDR2 sequences and a library of Non-human VL-CDR3

Step 10: PCR assembly via overlap PCR of DNA fragments derived from steps 8 and 9 via their common human VH-FR4 sequence Therefore, a novel mass humanized library of scFv fragments comprising non-human CDR3 regions is generated.

Optionally, the library may be cloned into a suitable display vector in a subsequent step.

Step 11: Cloning of the assembled scFv library in a phage display vector, or into another suitable display vector, such as a vector for ribosome display, or yeast display.

In a yet further preferred embodiment, the diversified non-human-derived CDR3 amino acid sequences or the amino acid sequence further encompassing 1, 2, or 3 amino acids N-terminal and/or C-terminal of the non-human-derived CDR3 amino acid sequence encode light chain CDR3 (CDR L3) sequences. In a particularly preferred embodiment, the light chain CDR3 (CDR L3) sequences have a length of between 5 to 20 amino acids, even more preferably between 7 and 13 amino acids.

In some embodiments, the nucleic acids encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a non-human CDR1 or CDR2, respectively, wherein at least some of the nucleic acid sequences encoding a CDR1 or CDR2 amino acid sequence have been modified to encode at least one amino acid present in non-human CDR1 or CDR2 amino acid sequences, respectively, in case of human CDR1 or CDR2, respectively, or to encode at least one amino acid present in human CDR1 or CDR2 amino acid sequences, respectively, in case of non-human CDR1 or CDR2, respectively.

A suitable method for obtaining diversified CDR1 and CDR2 sequences according to the disclosure encompass computationally integrating a plurality, such as $10^4$, $10^5$, or $10^6$-$10^7$ of simulated humanizations across the non-human antibody repertoire and the human acceptor antibody repertoire, in order to generate a mathematically optimal Bayesian representation of the humanization space between non-human and human, converting the probabilistic model to a frequentist interpretation, thereby obtaining a population or library. Each position ends up containing a probability of encountering the human germline residue, the non-human germline residues, and the most common collection of affinity maturation residues from both species. A map can be generated between every observed antibody in the non-human species and every preferred acceptor scaffold in humans. All sequences from both species can then be analyzed to: (1) obtain an optionally non-redundant database of amino acid sequences from both species from at least the memory B cell repertoire; (2) identify preferred human acceptor scaffolds for each non-human variable gene; (3) generate a positional weight matrix (PWM) of amino acid positional variability in the CDR1 and CDR2 of the non-human species and the human species by calculating the relative frequency of each amino acid at each position of a specific non-human variable gene and each member of the subset of preferred acceptor scaffolds from humans (see e.g. FIG. 3); (4) blend each of two PWMs (from one or more amino acids) from the non-human variable gene and a variable gene from the human preferred acceptor scaffolds to produce a hybrid PWM that contains the amino acid variation observed from both species at each position; (4) optionally adjust the blended PWM to remove cysteine, methionine, and tryptophan residues in order to generate superior therapeutics; and (5) optionally adjust the composition of the blended PWM to bias the library more towards either the human or non-human molecules, as well as to adjust the effective diversity of the library. In some embodiments, amino acid contributions from the human and non-human species are weighted evenly. In some embodiments the frequencies are altered such that in any combination of a set of amino acids from a collection of CDR sequences, a set of non-human example antibodies would occur at a frequency greater than the inverse of the size of the library or a predetermined set threshold. The set of amino acids from a collection of CDR sequences can be 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids, 30 amino acids, 31 amino acids, 32 amino acids, 33 amino acids, 34 amino acids, 35 amino acids, 36 amino acids, 37 amino acids, 38 amino acids, 39 amino acids, or 40 amino acids. In some embodiments the predetermined set threshold can be 10e-6, 10e-7, 10e-8, or 10e-9. In some embodiments, the human or non-human amino acid contributions are weighted so as to increase their representation relative to the other, such as by about or more than about 0.1%, 1%, 2%, 3%, 4%, 5%, 6%, 7%, 8%, 9%, 10%, 15%, 20%, 25%, or more. The PWMs can be converted to instructions to produce a library of nucleic acid molecules encoding immunoglobulin molecules. Nucleic acid synthesis instructions are generated such that each amino acid is encoded at a position at approximately its frequency within the PWM, with the frequency of each amino acid position independent of the others. The in silico nucleic acid library produced by these methods can be analyzed by probabilistic simulation to analyze the predicted properties of the synthesized library. The expected frequency of every molecule in the library can be calculated. Mathematical simulation can be used to explore the theoretical humanization of non-human antibodies to evaluate the proximity of the closest humanizations, and the blended PWM can be adjusted to bias the libraries towards a given level of humanization. This can be accomplished by iterative Monte Carlo sampling or other methods.

In a preferred embodiment, cysteine, and/or methionine residues are removed and/or the asparagine residue content is reduced, as these residues form biochemical liabilities.

By analyzing the CDR1 and CDR2 repertoires of non-human and human, respectively, it was possible to identify and generate CDR1 and CDR2 diversified sequences that span non-human germline, human germline, non-human somatic hypermutation, human somatic hypermutation, and non-human gene conversion at every position in CDR-H1, CDR-H2, CDR-L1, and CDR-L2. The resulting population or library thus is a novel entity with surprisingly beneficial properties, that is neither non-human nor human, but a hybrid repertoire exploring the space between.

Therefore, in a yet further preferred embodiment, the human or non-human CDR1 regions and the human and non-human CDR2 regions, on which the diversified CDR1 and CDR2 amino acid sequences are based, are selected from human germline CDR1 regions, human germline CDR2 regions, non-human germline CDR1 regions, non-human germline CDR2 regions, human somatic hypermutation CDR1 regions, human somatic hypermutation CDR2 regions, non-human somatic hypermutation CDR1 regions, non-human somatic hypermutation CDR2 regions, non-human gene conversion CDR1 regions, and non-human gene conversion CDR2 regions.

In a yet further preferred embodiment, the diversified CDR1 and CDR2 amino acid sequences are CDR-H1, CDR-H2, CDR-L1 and/or CDR-L2 sequences.

In a preferred embodiment, the population includes at least one nucleic acid encoding a human CDR-H1, and/or a human CDR-H2, and/or a human CDR-L1 and/or a human CDR-L2 sequence.

In a further preferred embodiment, the population includes at least one nucleic acid encoding a non-human CDR-H1, and/or a non-human CDR-H2, and/or a non-human CDR-L1 and/or a non-human CDR-L2 sequence.

In some embodiments, the human FR1, FR2, FR3 and FR4 regions are human framework regions selected to provide a scaffold conducive for non-human CDR3 amino acid sequences, with the proviso that the two C-terminal amino acids of FR2 are optionally non-human, and that the two C-terminal amino acids of FR3 are optionally non-human.

Therefore, in one preferred embodiment, the population comprises at least one nucleic acid encoding a human FR1, a human FR2, a human FR3 and a human FR4 region, and a human CDR1, and a human CDR2 region.

In another preferred embodiment, the population comprises at least one nucleic acid encoding a human FR1, a human FR2, a human FR3 and a human FR4 region, and a non-human CDR1, and a non-human CDR2 region.

Therefore, in yet another preferred embodiment, the population does not contain a nucleic acid encoding a human FR1, a human FR2, a human FR3 and a human FR4 region, and a human CDR1, and a human CDR2 region.

Therefore, in yet another preferred embodiment, the population does not contain a nucleic acid encoding a human FR1, a human FR2, a human FR3 and a human FR4 region, and a non-human CDR1, and a non-human CDR2 region.

A suitable scaffold conducive for non-human CDR3 amino acid sequences may be obtained by selecting a framework set by performing the following steps:
  computational imputation of germline repertoire element centroids which are most utilized in functional non-human antibodies
  generating an amino acid alignment of human frameworks compared to said computationally imputed non-human frameworks and selecting the closest representatives, respectively, that have the same length of CDR-H1, CDR-H2, CDR-L1, and CDR-L2 and similar sequence composition, respectively,
  further reducing the number of candidates framework sequences by preferring templates that are known to be stable in the art and optionally have worked as previous drugs,
  further reducing the number of framework candidates by structurally modeling antibodies from non-human and human using these frameworks and analyzing their structural superposition tolerance by root mean squared deviation (RMSD), and
  selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

As an example, a set of 2 heavy chain and 2 light chain frameworks comprising set of FR1, FR2, FR3 and FR4 regions respectively, can be selected. Moreover, the two C-terminal amino acids of heavy chain FR2 are optionally non-human, and the two C-terminal amino acids of heavy chain FR3 are optionally non-human, for example in case an SDR is grafted into a scaffold, or in case amino acids surrounding FR2 are substituted, as described above.

Therefore, in a yet further preferred embodiment, the human FR1, FR2, FR3 and FR4 regions which are human framework regions selected to provide a scaffold conducive for non-human CDR3 amino acid sequences are obtainable by:
  (i) providing
  (a) a collection of sequences of naturally occurring human antibodies each comprising a set of human FR1, FR2, FR3 and FR4 regions; and
  (b) a collection of sequences of naturally occurring non-human antibodies each comprising a set of non-human FR1, FR2, FR3 and FR4 regions, and (ii) identifying a plurality of sets of human FR1, FR2, FR3 and FR4 regions which provide a scaffold conducive for non-human CDR3 amino acid sequences by
 determining the parameters framework homology, CDR cosmology, CDR lengths, CDR canonical structure, and adoption of comfortable heavy or light mount angles, and
 selecting sets of human FR1, FR2, FR3 and FR4 regions which exhibit high scores for the parameters,
and/or
 the two C-terminal amino acids of heavy chain FR2 are optionally non-human, and
 the two C-terminal amino acids of heavy chain FR3 are optionally non-human.

In a further embodiment, the present disclosure provides a population of nucleic acids encoding at least one protein comprising at least one immunoglobulin variable domain having a non-human-derived CDR3 amino acid sequence embedded in essentially human framework sequences, obtainable by a method described herein.

Such population preferably represents a library of non-human CDR3 sequences, wherein mass humanization of the non-human antibodies is achieved.

It is understood that the preferred embodiments described for the methods of the disclosure also apply for the populations obtained thereby, and uses thereof.

In a preferred embodiment, a nucleic acid of the population is located in a vector. Such vector allows easy and efficient replication, cloning, selection and/or display, depending on the properties of such vector. Accordingly, a vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, Molecular Cloning. A Laboratory Manual, 2d edition, Cold Spring Harbor Laboratory, New York (1989)). In one embodiment, the vector is a viral vector. Viral vectors include, but are not limited to, retroviral and adenoviral vectors.

Suitable host cells or cell lines for transfection include bacterial cells. For example, the various strains of *E. coli* are well-known as host cells in the field of biotechnology. Various strains of *B. subtilis, Pseudomonas, Streptomyces*, and other bacilli and the like may also be employed. Many strains of yeast cells known to those skilled in the art are also available as host cells for expression of peptides disclosed herein. Other fungal cells or insect cells such as *Spodoptera frugipedera* (Sf9) cells may also be employed as expression systems. Alternatively, mammalian cells, such as human 293 cells, Chinese hamster ovary cells (CHO), the monkey COS-1 cell line or murine 3T3 cells derived from Swiss, BALB/c or NIH mice may be used. Still other suitable host cells, as well as methods for transfection, culture, amplification, screening, production, and purification are known in the art.

The host cells can be transfected, e.g. by conventional means such as electroporation with at least one expression vector containing a nucleic acid of the population of the disclosure under the control of a transcriptional regulatory sequence. The transfected or transformed host cell is then cultured under conditions that allow expression of the protein. The expressed protein(s) is(are) recovered, isolated, and optionally purified from the cell or from the culture medium, if expressed extracellularly by appropriate means known to one of skill in the art. For example, the proteins are isolated in soluble form following cell lysis, or extracted using known techniques, e.g. in guanidine chloride. If desired, the proteins are produced as a fusion protein, in particular in case display of the proteins is intended. The proteins may be further purified using any of a variety of conventional methods including, but not limited to: liquid chromatography such as normal or reversed phase, using HPLC, FPLC and the like; affinity chromatography such as with inorganic ligands or monoclonal antibodies; size exclusion chromatography; immobilized metal chelate chromatography; gel electrophoresis; and the like. One of skill in the art may select the most appropriate isolation and purification techniques.

In a more preferred embodiment, the nucleic acids are comprised in an expression vector suitable for display of the protein encoded by the nucleic acid on a virus, a cell or a surface. Typically, the nucleic acids encode fusion proteins comprising a protein comprising at least one immunoglobulin variable domain having a non-human-derived CDR3 amino acid sequence embedded in essentially human framework sequences and a protein sequence which allows display on a virus, a cell or a surface.

In a further embodiment, the present disclosure proves a population of proteins comprising at least one immunoglobulin variable domain having a non-human-derived CDR3 amino acid sequence embedded in essentially human framework sequences, obtainable by
 (i) expressing at least one protein encoded by the population described above in a suitable expression system, and
 (ii) optionally displaying at least one protein on a virus, a cell or a surface.

The cell is preferably a bacterial cell or a eukaryotic cell, such as a yeast cell.

The preferred embodiments for methods of the disclosure also apply to populations of proteins described herein.

In a further embodiment, the present disclosure provides a population of proteins comprising at least one immunoglobulin variable domain having a non-human-derived CDR3 amino acid sequence embedded in essentially human framework sequences, obtainable by
 (i) expressing at least one protein encoded by a population as described above in a suitable expression system, and
 (ii) displaying at least one protein on a virus, a cell or a surface.

Preferably, at least 2, 3, 4, 5, 6, 7, 8, 9, 10, 50, 100, 150, 200 or more proteins encoded by a population of the present disclosure are expressed in a suitable expression system.

In a more preferred embodiment, at least 2, 3, 4, 5, 6, 7, 8, 9, 10, 50, 100, 150, 200 or more proteins encoded by a population of the disclosure are displayed on a virus, a cell or a surface, preferably wherein the proteins are fusion proteins, such as a fusion protein to a minor coat protein of a bacterial phage or to Agap2p.

A number of display techniques are known in the art, which enable a connection between genotype and binding properties of the antibodies. For example, display may be achieved by phage display, yeast display, bacterial display, ribosome display mRNA. In some embodiments, the display technique is phage display. In a typical phage display, the protein comprising the antigen of interest is expressed as a polypeptide fusion to a bacteriophage coat protein and subsequently screened by binding to immobilized or soluble biotinylated ligand (e.g., Huse et al., '89; Clackson et al., '91; Marks et al., '92). Fusions are made most commonly to a minor coat protein, called the gene III protein (pIII), which is present in three to five copies at the tip of the phage. A phage constructed in this way can be considered a compact genetic "unit," possessing both the phenotype (binding activity of the displayed antibody) and genotype (the gene coding for that antibody) in one package. Phage display has been successfully applied to antibodies, DNA binding proteins, protease inhibitors, short peptides, and enzymes.

Antibodies possessing desirable binding properties are preferably selected by binding to immobilized antigen in a process called "panning". Phage-bearing nonspecific antibodies are removed by washing, and then the bound phage are eluted and amplified by infection of E. coli. This approach has been applied to generate antibodies against many antigens.

Yeast display methods are well-known to a skilled person and are for example described in WO 99/36569. Typically, fusion proteins comprising the yeast protein Aga2p are used for displaying the proteins of interest at the cell surface.

Ribosome display techniques are also known in the art and are for example described in Hanes, J.; Plückthun, A. (1997; Proc. Natl. Acad. Sci. U.S.A. 94 (10): 4937-42) and He M. and Taussig M. J. (2007; Nature Methods 4 (3): 281-288).

In a further embodiment, the present disclosure provides a library comprising a plurality, preferably 2, 3, 4, 5, 6, 7, 8, 9, 10, 50, 100, 150, 200, $10^3$, $10^4$, $10^5$, $10^6$ or more of replicable genetic packages, that are capable of displaying at least 1, 2, 3, 4, 5, 6, 7, 8, 9, 10, 50, 100, 150, 200 or more proteins encoded by a population of the disclosure on a virus, a cell or a surface.

In a further embodiment, the present disclosure provides a library comprising a plurality, preferably 2, 3, 4, 5, 6, 7, 8, 9, 10, 50, 100, 150, 200, $10^3$, $10^4$, $10^5$, $10^6$ or more of replicable genetic packages, that display at least 1, 2, 3, 4, 5, 6, 7, 8, 9, 10, 50, 100, 150, 200 or more proteins encoded by a population of the disclosure on a virus, a cell or a surface.

A replicable genetic package is understood as a biological complex comprising a nucleic acid, and at least one peptide encoded by the nucleic acid. Examples of replicable genetic packages include cells, spores, bacteria, viruses and bacteriophage. Thus, the particular replicable genetic package or library thereof can be selected from any one of the foregoing and/or include different combinations thereof. Replicable genetic packages are capable of replication either by self-replication, in combination with a host and/or a helper virus, or by in vitro replication, transcription and expression.

Bacteriophages including phagemids are preferred replicable genetic packages. Preferred phage are the filamentous phage (e.g., M13, fd and fl) and phagemid vectors derived therefrom. See, WO 91/19818; WO 91/18989; WO 92/01047; WO 92/06204; WO 92/18619. Other phage of E. coli, such as T7 phage, or phage of other bacterial species can also be used. Filamentous phages are 6 nm in diameter and up to one micron in length. It has been used extensively in peptide phage display. Its surface consists of five coat proteins, two of which, pIII and pVIII, have been used to display peptide libraries, pIII contains 406 amino acids and is present in three to five copies. The major coat protein, pVIII, which contains 50 amino acids, constitutes the bulk of the phage protein as it is present in approximately 2700 copies. The bacteriophage can also be a non-filamentous phage such as icosahedral phages T7 and lambda. The major coat protein of T7 phage is the gene 10 capsid protein, which contains 370 amino acids and is present in 415 copies.

In addition to phage, a replicable genetic package of the disclosure can include eukaryotic viruses (e.g. the Moloney murine leukemia virus; see, e.g., Han, et al., Proc. Natl. Acad. Sci. USA 92:9747-9751 (1995)) or spores (e.g. spores from B. subtilis; see, e.g., Donovan, et al., J. Mol. Biol. 196:1-10 (1987)). A variety of different cells can also be used as replicable genetic packages. Examples of suitable bacterial cells include, but are not limited to, *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli*.

In a yet further embodiment, the present disclosure provides a method for screening for at least one protein comprising at least one immunoglobulin variable domain, in particular antibodies or fragments thereof, in particular selected from Fab, scFv and Fv, which specifically binds to an antigen of interest, comprising the following steps:

a) providing a library comprising a plurality, preferably 2, 3, 4, 5, 6, 7, 8, 9, 10, 50, 100, 150, 200, $10^3$, $10^4$, $10^5$, $10^6$ or more of replicable genetic packages that display at least 1, 2, 3, 4, 5, 6, 7, 8, 9, 10, 50, 100, 150, 200 or more proteins encoded by a population of the disclosure on a virus, a cell or a surface, b) contacting the library of a) with at least one antigen of interest or a fragment thereof comprising at least one potential epitope, c) isolating at least one genetic package which exhibits the desired binding property, in particular affinity, and d) optionally determining the sequence or part of the sequence of the nucleic acid encoding the protein comprising at least one immunoglobulin variable domain, e) optionally repeating steps a) to d) one or more times with 2 or more genetic packages isolated in step c).

As explained above, affinity to the antigen may be determined. For example, this can be performed by surface plasmon resonance spectroscopy, e.g. using a Biacore apparatus. For example, proteins exhibiting an affinity (Kd) of $10^{-6}$, $10^{-7}$, $10^{-8}$, $10^{-9}$ or less may be selected and optionally used in further screening rounds.

In a yet further embodiment, a method of the present disclosure may be repeated one or more times, for example 1, 2, 3, 4, 5 or more times. Thereby, additional selection rounds are performed.

In a preferred embodiment, at least 2 of the displayed proteins have different CDR3 amino acid sequences, in particular different CDR-3H and/or CDR-3L amino acid sequences, more preferably wherein at least 2, 3, 4, 5, 6, 7, 8, 9, 10, 50, 100, 150, 200 or more of the displayed proteins have different CDR3 amino acid sequences, in particular different CDR-3H and/or CDR-3L amino acid sequences, and/or wherein at least 50%, at least 80%, at least 90%, at least 95%, at least 96%, at least 97%, at least 98%, at least 99% or 100% of the nucleic acids of the of the displayed proteins have different CDR3 amino acid sequences, in particular different CDR-3H and/or CDR-3L amino acid sequences.

In a further embodiment, the present disclosure provides a population of nucleic acids encoding at least one protein comprising at least one immunoglobulin variable domain having a non-human-derived CDR3 amino acid sequence embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a non-human-derived CDR3 amino acid sequence; wherein the nucleic acid sequences encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based (i) on a nucleic acid sequence encoding a human CDR1 or CDR2, respectively, or (ii) on a nucleic acid sequence encoding a non-human CDR1 or CDR2, respectively; wherein at least some of the nucleic acid sequences encoding a CDR1 or CDR2 amino acid sequence have been modified to encode at least one amino acid present in non-human CDR1 or CDR2 amino acid sequences, respectively, in case of human CDR1 or CDR2, respectively, or to encode at least one amino acid present in human CDR1 or CDR2 amino acid sequences, respectively, in case of non-human CDR1 or CDR2, respectively; and wherein the human FR1, FR2, FR3 and FR4 regions are human framework regions selected to provide a scaffold conducive for non-human CDR3 amino acid sequences, with the proviso: that the two C-terminal amino acids of FR2 are optionally non-human, and that the two C-terminal amino acids of FR3 are optionally non-human.

It is understood that the preferred embodiments for the methods of the disclosure also apply to the populations of nucleic acids described herein.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. In some embodiments, the FR1 and FR4 regions are human FR1 and FR4 regions. As also described above, it is possible that a nucleic acid encoding a non-human-derived CDR3 amino acid sequence, preferably a non-human-CDR3 amino acid sequence, further comprising 1, 2, or 3 amino acids N-terminal of the non-human-derived CDR3 amino acid sequence, and/or 1, 2, or 3 amino acids C-terminal of the non-human-derived CDR3 amino acid sequence is embedded, in particular in case a nucleic acid encoding a non-human SDR is embedded. For example an SDR comprising the CDR-3H may be embedded.

The N-terminal "C" is also present in human heavy FR3 sequences, and the C-terminal "W" is also present in human heavy FR4 sequences. Accordingly, in case the FR3 and FR4 regions are interspaced by a non-human-derived CDR3 amino acid sequence of the structure CAR|XXXXXXXXXXDY|W (SEQ ID NO: 1), the resulting FR3 heavy region will contain the C-terminal non-human amino acids "AR", whereas the remaining parts of the FR3 heavy region will be human, and the FR4 heavy region will be human.

Therefore, in another preferred embodiment, at least one nucleic acid encoding a non-human CDR3 sequence is embedded, such that the human FR3 and FR4 regions are interspaced by a non-human CDR3 amino acid sequence. Preferably, also the resulting FR3 and FR4 regions will be human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

In particular, the two positions N-terminal to CDR-H2 (i.e. positions X10 and X11) may be "VS" in the human:

CDR-H2: GLEWVS |X12X13X14X15X16X17X18X19 X20X21X22X23DSVKG| RFT (SEQ ID NO: 2)

In one preferred embodiment, V and/or S at positions X10 and X11 are independently non-human, preferably non-human, in the heavy FR2 region.

In a further preferred embodiment, at least 2, 3, 4, 5, 6, 7, 8, 9, 10, 50, 100, 150, 200 or more nucleic acids of the population exhibit different amino acids at the two C-terminal amino acids of human FR2, more preferably at positions X10 and X11 of heavy human FR2.

In a further preferred embodiment, the population of nucleic acids encodes proteins comprising at least a VH domain and/or at least one VL domain, more preferably the nucleic acids encode an antibody, an scFv, a Fv or Fab.

The nucleic acids encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a non-human CDR1 or CDR2, respectively, wherein at least some of the nucleic acid sequences encoding a CDR1 or CDR2 amino acid sequence have been modified to encode at least one amino acid present in non-human CDR1 or CDR2 amino acid sequences, respectively, in case of human CDR1 or CDR2, respectively, or to encode at least one amino acid present in human CDR1 or CDR2 amino acid sequences, respectively, in case of non-human CDR1 or CDR2, respectively.

A diversified CDR1 and CDR2 sequences can be obtained by computationally integrating a plurality, such as $10^4$, $10^5$, or $10^6$-$10^7$ of simulated humanizations across the non-human antibody repertoire and the human acceptor antibody repertoire, in order to generate a mathematically optimal Bayesian representation of the humanization space between non-human and human, converting the probabilistic model to a frequentist interpretation, thereby obtaining a population or library. Each position ends up containing a probability of encountering the human germline residue, the non-human germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment, the human or non-human CDR1 regions and the human and non-human CDR2 regions, on which the diversified CDR1 and CDR2 amino acid sequences are based, are selected from human germline CDR1 regions, human germline CDR2 regions, non-human germline CDR1 regions, non-human germline CDR2 regions, human somatic hypermutation CDR1 regions, human somatic hypermutation CDR2 regions, non-human somatic hypermutation CDR1 regions, non-human somatic hypermutation CDR2 regions, non-human gene conversion CDR1 regions, and non-human gene conversion CDR2 regions.

In a yet further preferred embodiment, the diversified CDR1 and CDR2 amino acid sequences are CDR-H1, CDR-H2, CDR-L1 and/or CDR-L2 sequences.

In a preferred embodiment, the population includes at least one nucleic acid encoding a human CDR-H1, and/or a human CDR-H2, and/or a human CDR-L1 and/or a human CDR-L2 sequence.

In a further preferred embodiment, the population includes at least one nucleic acid encoding a non-human CDR-H1, and/or a non-human CDR-H2, and/or a non-human CDR-L1 and/or a non-human CDR-L2 sequence.

In some embodiments, the human FR1, FR2, FR3 and FR4 regions are human framework regions selected to provide a scaffold conducive for non-human CDR3 amino acid sequences, with the proviso that the two C-terminal amino acids of FR2 are optionally non-human, and that the two C-terminal amino acids of FR3 are optionally non-human. In one preferred embodiment, a population of the disclosure comprises at least one nucleic acid encoding a human FR1, a human FR2, a human FR3 and a human FR4 region, and a human CDR1, and a human CDR2 region.

In another preferred embodiment, a population of the disclosure comprises at least one nucleic acid encoding a human FR1, a human FR2, a human FR3 and a human FR4 region, and a non-human CDR1, and a non-human CDR2 region.

In yet another preferred embodiment, a population of the disclosure does not contain a nucleic acid encoding a human FR1, a human FR2, a human FR3 and a human FR4 region, and a human CDR1, and a human CDR2 region.

In yet another preferred embodiment, a population of the disclosure does not contain a nucleic acid encoding a human FR1, a human FR2, a human FR3 and a human FR4 region, and a non-human CDR1, and a non-human CDR2 region.

A suitable scaffold conducive for non-human CDR3 amino acid sequences is obtainable by selecting a framework set by performing the following steps:
  computational imputation of germline repertoire element centroids which are most utilized in functional non-human antibodies
  generating an amino acid alignment of human frameworks compared to said computationally imputed non-human frameworks and selecting the closest representatives, respectively, that have the same length of CDR-H1, CDR-H2, CDR-L1, and CDR-L2 and similar sequence composition, respectively,
  further reducing the number of candidates framework sequences by preferring templates that are known to be stable in the art and optionally have worked as previous drugs,
  further reducing the number of framework candidates by structurally modeling antibodies from non-human and human using these frameworks and analyzing their structural superposition tolerance by root mean squared deviation (RMSD), and
  selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

As an example, a set of 2 heavy chain and 2 light chain frameworks comprising set of FR1, FR2, FR3 and FR4 regions respectively, can be present. Moreover, the two C-terminal amino acids of heavy chain FR2 may optionally be non-human, and the two C-terminal amino acids of heavy chain FR3 may optionally be non-human, for example in case a specificity determining residue (SDR) is grafted into a scaffold, or in case amino acids surrounding FR2 are substituted, as described above.

In a yet further preferred embodiment, the human FR1, FR2, FR3 and FR4 regions which are human framework regions selected to provide a scaffold conducive for non-human CDR3 amino acid sequences are obtainable by:
  (i) providing
    (a) a collection of sequences of naturally occurring human antibodies each comprising a set of human FR1, FR2, FR3 and FR4 regions; and
    (b) a collection of sequences of naturally occurring non-human antibodies each comprising a set of non-human FR1, FR2, FR3 and FR4 regions, and
  (ii) identifying a plurality of sets of human FR1, FR2, FR3 and FR4 regions which provide a scaffold conducive for non-human CDR3 amino acid sequences by
    determining the parameters framework homology, CDR cosmology, CDR lengths, CDR canonical structure, and adoption of comfortable heavy or light mount angles, and
    selecting sets of human FR1, FR2, FR3 and FR4 regions which exhibit high scores for the parameters,
    and/or
    the two C-terminal amino acids of heavy chain FR2 are optionally non-human, and
    the two C-terminal amino acids of heavy chain FR3 are optionally non-human.

In a further embodiment, the present disclosure provides a population of proteins comprising at least one immunoglobulin variable domain having a non-human-derived CDR3 amino acid sequence embedded in essentially human framework sequences, and wherein the proteins further comprise at least one moiety allowing display of the at least one protein on a virus, a cell, or a surface.

Suitable moieties, in particular protein moieties allowing display are known in the art and described herein, such as Aga2p and pIII.

The cell is preferably a bacterial cell or a eukaryotic cell, such as a yeast cell.

In a preferred embodiment, at least 2 of the nucleic acids of the population encode different CDR3 amino acid sequences, in particular different CDR-3H and/or CDR-3L amino acid sequences, more preferably wherein at least 2, 3, 4, 5, 6, 7, 8, 9, 10, 50, 100, 150, 200 or more encode different CDR3 amino acid sequences, in particular different CDR-3H and/or CDR-3L amino acid sequence, and/or wherein at least 50%, at least 80%, at least 90%, at least 95%, at least 96%, at least 97%, at least 98%, at least 99% or 100% of the nucleic acids of the population encode different CDR3 amino acid sequences, in particular different CDR-3H and/or CDR-3L amino acid sequences. In a more preferred embodiment the, sequences are diversified due to immunization of one or more non-humans with a target of interest. Preferably, the sequences are diversified within the CDR3 amino acid sequence, in case the sequence further encompasses 1, 2, or 3 amino acids N-terminal and/or C-terminal of the non-human-derived CDR3 amino acid sequence.

A population of nucleic acids of the disclosure is particularly useful for mass humanization of non-human antibodies and subsequent screening for antibodies for suitable binding properties for an antigen of interest.

By expressing the population of nucleic acids in a suitable expression system for display, a population of displayed, mass humanized proteins, in particular antibodies or antibody fragments such as scFv, Fv or Fab is obtained, which contain non-human CDR3 or non-human-derived CDR3 regions.

In a further embodiment, the present disclosure provides a population of proteins comprising at least one immunoglobulin variable domain having a non-human-derived CDR3 amino acid sequence embedded in essentially human framework sequences, obtainable by
  (i) expressing at least one protein encoded by a population of the disclosure above in a suitable expression system, and
  (ii) displaying at least one protein on a virus, a cell or a surface.

Preferably, at least 2, 3, 4, 5, 6, 7, 8, 9, 10, 50, 100, 150, 200 or more proteins encoded by a population of the disclosure are expressed in a suitable expression system.

In a more preferred embodiment, at least 2, 3, 4, 5, 6, 7, 8, 9, 10, 50, 100, 150, 200 or more proteins encoded by a population of the disclosure are displayed on a virus, a cell or a surface, preferably wherein the proteins are fusion proteins, such as a fusion protein to a minor coat protein of a bacterial phage or to Agap2p.

By expressing the population of nucleic acids in a suitable expression system a population of mass humanized proteins, in particular antibodies or antibody fragments such as scFv, Fv or Fab is obtained, which contain non-human CDR3 or non-human-derived CDR3 regions.

In some embodiments, the present disclosure provides a population of proteins comprising at least one immunoglobulin variable domain having a non-human-derived CDR3 amino acid sequence embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a non-human-derived CDR3 amino acid sequence; wherein the CDR1 and CDR2 amino acid sequences are diversified among the population of proteins comprising at least one immunoglobulin variable domain, wherein each CDR1 or CDR2 amino acid sequence is independently based (i) on a human CDR1 or CDR2, respectively, or (ii) on a non-human CDR1 or CDR2, respectively; wherein at least some of the CDR1 or CDR2 amino acid sequences have been modified to comprise at least one amino acid present in non-human CDR1 or CDR2 amino acid sequences, respectively, in case of human CDR1 or CDR2, respectively, or to comprise at least one amino acid present in human CDR1 or CDR2 amino acid sequences, respectively, in case of non-human CDR1 or CDR2, respectively; and wherein the human FR1, FR2, FR3 and FR4 regions are human framework regions selected to provide a scaffold conducive for non-human CDR3 amino acid sequences, with the proviso: that the two C-terminal amino acids of FR2 are optionally non-human, and that the two C-terminal amino acids of FR3 are optionally non-human.

The populations or libraries of the disclosure are particularly suitable for mass humanization of non-human antibodies and allow for generalizing the humanization process by providing scaffolds that represent the codified landscape of all intermediate humanization across non-human and human with a population or library that explores the space between both species.

In a preferred embodiment, the present disclosure provides a population of proteins comprising at least one immunoglobulin variable domain having a non-human-derived CDR3 amino acid sequence embedded in essentially human framework sequences as described above, wherein the at least one protein comprising at least one immunoglobulin variable domain having a non-human-derived CDR3 amino acid sequence embedded in essentially human framework sequences; comprises a VH domain, or a VL domain, or a VH domain and a VL domain, or a heavy chain of an antibody or a fragment thereof comprising the VH domain, and/or a light chain of an antibody or a fragment thereof comprising the VL domain and/or an scFv, more preferably an scFv; and/or is selected from an immunoglobulin molecule, a disulfide linked Fv, a monoclonal antibody, an scFv, a single domain antibody, a diabody, a multispecific antibody, a Fab, a Fab', a bispecific antibody, a F(ab')2, or an Fv, more preferably an scFv; and wherein the at least one protein optionally further comprises at least one moiety allowing display of the at least one protein on a virus, a cell, or a surface.

In a more preferred embodiment, the at least one protein optionally further comprises at least one moiety allowing display of the at least one protein on a virus, a cell, or a surface. Such moieties allowing display are described herein.

In a further preferred embodiment, the present disclosure provides a population of proteins comprising at least one immunoglobulin variable domain having a non-human-derived CDR3 amino acid sequence embedded in essentially human framework sequences as described above, wherein the at least one protein comprising at least one immunoglobulin variable domain having a non-human-derived CDR3 amino acid sequence embedded in essentially human framework sequences, wherein one or more, preferably 1, 2, 3, or 4, different sets of framework regions comprising a first human framework region (FR1), a second human framework region (FR2), a third human framework region (FR3), and a fourth human framework region (FR4) are present in the VH domains, and/or one or more, preferably 1, 2, 3, or 4, different sets of framework regions comprising a first human framework region (FR1), a second human framework region (FR2), a third human framework region (FR3), and a fourth human framework region (FR4) are present in the VL domains,
  with the proviso:
    that the two C-terminal amino acids of FR2 are optionally non-human, and
    that the two C-terminal amino acids of FR3 are optionally non-human.

It is understood that the preferred embodiments for the methods of the disclosure also apply to the populations of proteins described herein.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. In some embodiments, the FR1 and FR4 regions are human FR1 and FR4 regions. As also described above, it is possible that a non-human-derived CDR3 amino acid sequence, preferably a non-human-CDR3 amino acid sequence, further comprising 1, 2, or 3 amino acids N-terminal of the non-human-derived CDR3 amino acid sequence, and/or 1, 2, or 3 amino acids C-terminal of the non-human-derived CDR3 amino acid sequence is embedded, in particular in case a non-human SDR is embedded. For example an SDR comprising the CDR-3H may be embedded. In such embodiment, the following further N-terminal and C-terminal amino acids, respectively, are present:

CAR |XXXXXXXXXXDY| W (SEQ ID NO: 1)

Therefore, in another preferred embodiment, at least one non-human CDR3 sequence is embedded, such that the human FR3 and FR4 regions are interspaced by a non-human CDR3 amino acid sequence. Preferably, also the resulting FR3 and FR4 regions will be human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

In a further preferred embodiment, the proteins of the population comprise at least one VH domain and/or at least one VL domain, more preferably the proteins comprise or represent an antibody, an scFv, a Fv or Fab.

The CDR1 and CDR2 amino acid sequences are diversified among the population of proteins comprising at least one immunoglobulin variable domain, wherein each CDR1 or CDR2 amino acid sequence is independently based i) on a human CDR1 or CDR2, respectively, or ii) on a non-human CDR1 or CDR2, respectively, wherein at least some of the CDR1 or CDR2 amino acid sequences have been modified to contain at least one amino acid present in non-human CDR1 or CDR2 amino acid sequences, respectively, in case of human CDR1 or CDR2, respectively, or to contain at least one amino acid present in human CDR1 or CDR2 amino acid sequences, respectively, in case of non-human CDR1 or CDR2, respectively.

Diversified CDR1 and CDR2 sequences according to the disclosure can be obtained by computationally integrating a plurality, such as $10^4$, $10^5$, or $10^6$-$10^7$ of simulated humanizations across the non-human antibody repertoire and the human acceptor antibody repertoire, in order to generate a mathematically optimal Bayesian representation of the humanization space between non-human and human, converting the probabilistic model to a frequentist interpretation, thereby obtaining a population or library. Each position ends up containing a probability of encountering the human germline residue, the non-human germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment, the human or non-human CDR1 regions and the human and non-human CDR2 regions, on which the diversified CDR1 and CDR2 amino acid sequences are based, are selected from human germline CDR1 regions, human germline CDR2 regions, non-human germline CDR1 regions, non-human germline CDR2 regions, human somatic hypermutation CDR1 regions, human somatic hypermutation CDR2 regions, non-human somatic hypermutation CDR1 regions, non-human somatic hypermutation CDR2 regions, non-human gene conversion CDR1 regions, and non-human gene conversion CDR2 regions.

In a yet further preferred embodiment, the diversified CDR1 and CDR2 amino acid sequences are CDR-H1, CDR-H2, CDR-L1 and/or CDR-L2 sequences.

In a preferred embodiment, the population includes at least one human CDR-H1, and/or a human CDR-H2, and/or a human CDR-L1 and/or a human CDR-L2 sequence.

In a further preferred embodiment, the population includes at least one non-human CDR-H1, and/or a non-human CDR-H2, and/or a non-human CDR-L1 and/or a non-human CDR-L2 sequence.

In some embodiments, the human FR1, FR2, FR3 and FR4 regions are human framework regions selected to provide a scaffold conducive for non-human CDR3 amino acid sequences, with the proviso that the two C-terminal amino acids of FR2 are optionally non-human, and that the two C-terminal amino acids of FR3 are optionally non-human. In one preferred embodiment, the population of the disclosure comprises at least one protein comprising a human FR1, a human FR2, a human FR3 and a human FR4 region, and a human CDR1, and a human CDR2 region.

In another preferred embodiment, the population of the disclosure comprises at least one protein comprising a human FR1, a human FR2, a human FR3 and a human FR4 region, and a non-human CDR1, and a non-human CDR2 region.

In yet another preferred embodiment, the population of the disclosure does not contain a protein comprising a human FR1, a human FR2, a human FR3 and a human FR4 region, and a human CDR1, and a human CDR2 region.

In yet another preferred embodiment, the population of the disclosure does not contain a protein comprising a human FR1, a human FR2, a human FR3 and a human FR4 region, and a non-human CDR1, and a non-human CDR2 region.

A suitable scaffold conducive for non-human CDR3 amino acid sequences is obtainable by selecting a framework set by performing the following steps:

- computational imputation of germline repertoire element centroids which are most utilized in functional non-human antibodies
- generating an amino acid alignment of human frameworks compared to said computationally imputed non-human frameworks and selecting the closest representatives, respectively, that have the same length of CDR-H1, CDR-H2, CDR-L1, and CDR-L2 and similar sequence composition, respectively,
- further reducing the number of candidates framework sequences by preferring templates that are known to be stable in the art and optionally have worked as previous drugs,
- further reducing the number of framework candidates by structurally modeling antibodies from non-human and human using these frameworks and analyzing their structural superposition tolerance by root mean squared deviation (RMSD), and selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

For example, a set of 2 heavy chain and 2 light chain frameworks comprising set of FR1, FR2, FR3 and FR4 regions respectively, can be present. Moreover, the two C-terminal amino acids of heavy chain FR2 may optionally be non-human, and the two C-terminal amino acids of heavy chain FR3 may optionally be non-human, for example in case an SDR is grafted into a scaffold, or in case amino acids surrounding FR2 are substituted, as described above.

In a yet further preferred embodiment, the human FR1, FR2, FR3 and FR4 regions which are human framework regions selected to provide a scaffold conducive for non-human CDR3 amino acid sequences are obtainable by:
  (i) providing
  (a) a collection of sequences of naturally occurring human antibodies each comprising a set of human FR1, FR2, FR3 and FR4 regions; and
  (b) a collection of sequences of naturally occurring non-human antibodies each comprising a set of non-human FR1, FR2, FR3 and FR4 regions, and
  (ii) identifying a plurality of sets of human FR1, FR2, FR3 and FR4 regions which provide a scaffold conducive for non-human CDR3 amino acid sequences by
    determining the parameters framework homology, CDR cosmology, CDR lengths, CDR canonical structure, and adoption of comfortable heavy or light mount angles, and
    selecting sets of human FR1, FR2, FR3 and FR4 regions which exhibit high scores for the parameters,
  and/or
    the two C-terminal amino acids of heavy chain FR2 are optionally non-human, and
    the two C-terminal amino acids of heavy chain FR3 are optionally non-human.

In a preferred embodiment, at least 2 of the proteins of the population comprise different CDR3 amino acid sequences, in particular different CDR-3H and/or CDR-3L amino acid sequences,
  more preferably wherein at least 2, 3, 4, 5, 6, 7, 8, 9, 10, 50, 100, 150, 200 or more proteins comprise different CDR3 amino acid sequences, in particular different CDR-3H and/or CDR-3L amino acid sequence, and/or
  wherein at least 50%, at least 80%, at least 90%, at least 95%, at least 96%, at least 97%, at least 98%, at least 99% or 100% of the proteins comprise different CDR3 amino acid sequences, in particular different CDR-3H and/or CDR-3L amino acid sequences. In a more preferred embodiment the sequences are diversified due to immunization of one or more non-humans with a target of interest. Preferably, the sequences are diversified within the CDR3 amino acid sequence, in case the sequence further encompasses 1, 2, or 3 amino acids N-terminal and/or C-terminal of the non-human-derived CDR3 amino acid sequence.

A population of proteins of the disclosure is particularly useful for mass humanization of non-human antibodies and subsequent screening for antibodies for suitable binding properties for an antigen of interest.

Further, the disclosure provides for Acceptor framework libraries, which are suitable for methods and uses of the present disclosure.

In a further embodiment, the present disclosure provides a population of Acceptor Framework nucleic acid, wherein each Acceptor Framework nucleic acid comprises nucleic acids encoding a set of framework regions comprising a first human framework region (FR1), a second human framework region (FR2), a third human framework region (FR3), and a fourth human framework region (FR4); wherein the FR1 and FR2 regions are interspaced by a complementarity determining region 1 (CDR1), the FR2 and FR3 regions are interspaced by a complementarity determining region 2 (CDR2), and the nucleic acid sequences encoding FR3 and FR4 regions are linked directly or are interspaced by a stuffer nucleic acid sequence; and wherein the nucleic acid sequences encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based (i) on a nucleic acid sequence encoding a human CDR1 or CDR2, respectively, or (ii) on a nucleic acid sequence encoding a non-human CDR1 or CDR2, respectively; wherein at least some of the nucleic acid sequences encoding a CDR1 or CDR2 amino acid sequence have been modified to encode at least one amino acid present in non-human CDR1 or CDR2 amino acid sequences, respectively, in case of human CDR1 or CDR2, respectively, or to encode at least one amino acid present in human CDR1 or CDR2 amino acid sequences, respectively, in case of non-human CDR1 or CDR2, respectively; and wherein the human FR1, FR2, FR3 and FR4 regions are human framework regions selected to provide a scaffold conducive for non-human CDR3 amino acid sequences,
  with the proviso:
    that the two C-terminal amino acids of FR2 are optionally non-human, and
    that the two C-terminal amino acids of FR3 are optionally non-human.

It is understood that the preferred embodiments for the methods of the disclosure and populations of the disclosure also apply to the populations of Acceptor Framework nucleic acids described herein.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. In some embodiments, the FR1 and FR4 regions are human FR1 and FR4 regions. Preferably, the FR3 is human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

The nucleic acids encoding the CDR1 and CDR2 amino acid sequences are diversified among the population of Acceptor Framework nucleic acids, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a non-human CDR1 or CDR2, respectively, wherein at least some of the nucleic acid sequences encoding a CDR1 or CDR2 amino acid sequence have been modified to encode at least one amino acid present in non-human CDR1 or CDR2 amino acid sequences, respectively, in case of human CDR1 or CDR2, respectively, or to encode at least one amino acid present in human CDR1 or CDR2 amino acid sequences, respectively, in case of non-human CDR1 or CDR2, respectively.

Diversified CDR1 and CDR2 sequences according to the disclosure can be obtained by computationally integrating a plurality, such as $10^4$, $10^5$, or $10^6$-$10^7$ of simulated humanizations across the non-human antibody repertoire and the human acceptor antibody repertoire, in order to generate a mathematically optimal Bayesian representation of the humanization space between non-human and human, converting the probabilistic model to a frequentist interpretation, thereby obtaining a population or library. Each position ends up containing a probability of encountering the human germline residue, the non-human germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment, the human or non-human CDR1 regions and the human and non-human CDR2 regions, on which the diversified CDR1 and CDR2 amino acid sequences are based, are selected from human germline CDR1 regions, human germline CDR2 regions, non-human germline CDR1 regions, non-human germline CDR2 regions, human somatic hypermutation CDR1 regions, human somatic hypermutation CDR2 regions, non-human somatic hypermutation CDR1 regions, non-human somatic hypermutation CDR2 regions, non-human gene conversion CDR1 regions, and non-human gene conversion CDR2 regions.

In a yet further preferred embodiment, the diversified CDR1 and CDR2 amino acid sequences are CDR-H1, CDR-H2, CDR-L1 and/or CDR-L2 sequences.

In a preferred embodiment, the population includes at least one nucleic acid encoding a human CDR-H1, and/or a human CDR-H2, and/or a human CDR-L1 and/or a human CDR-L2 sequence.

In a further preferred embodiment, the population includes at least one nucleic acid encoding a non-human CDR-H1, and/or a non-human CDR-H2, and/or a non-human CDR-L1 and/or a non-human CDR-L2 sequence.

In some embodiments, the human FR1, FR2, FR3 and FR4 regions are human framework regions selected to provide a scaffold conducive for non-human CDR3 amino acid sequences, with the proviso that the two C-terminal amino acids of FR2 are optionally non-human, and that the two C-terminal amino acids of FR3 are optionally non-human. In one preferred embodiment, a population of the disclosure comprises at least one nucleic acid encoding a human FR1, a human FR2, a human FR3 and a human FR4 region, and a human CDR1, and a human CDR2 region.

In another preferred embodiment, a population of the disclosure comprises at least one nucleic acid encoding a human FR1, a human FR2, a human FR3 and a human FR4 region, and a non-human CDR1, and a non-human CDR2 region.

In yet another preferred embodiment, a population of the disclosure does not contain a nucleic acid encoding a human FR1, a human FR2, a human FR3 and a human FR4 region, and a human CDR1, and a human CDR2 region.

In yet another preferred embodiment, a population of the disclosure does not contain a nucleic acid encoding a human FR1, a human FR2, a human FR3 and a human FR4 region, and a non-human CDR1, and a non-human CDR2 region.

A suitable scaffold conducive for non-human CDR3 amino acid sequences is obtainable by selecting a framework set by performing the following steps:
 computational imputation of germline repertoire element centroids which are most utilized in functional non-human antibodies
 generating an amino acid alignment of human frameworks compared to said computationally imputed non-human frameworks and selecting the closest representatives, respectively, that have the same length of CDR-H1, CDR-H2, CDR-L1, and CDR-L2 and similar sequence composition, respectively,
 further reducing the number of candidates framework sequences by preferring templates that are known to be stable in the art and optionally have worked as previous drugs,
 further reducing the number of framework candidates by structurally modeling antibodies from non-human and human using these frameworks and analyzing their structural superposition tolerance by root mean squared deviation (RMSD), and
 selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

As an example, a set of 2 heavy chain and 2 light chain frameworks comprising set of FR1, FR2, FR3 and FR4 regions respectively, can be present. Moreover, the two C-terminal amino acids of heavy chain FR2 may optionally be non-human, and the two C-terminal amino acids of heavy chain FR3 may optionally be non-human, for example in case an SDR is grafted into a scaffold, or in case amino acids surrounding FR2 are substituted, as described above.

In a yet further preferred embodiment, the human FR1, FR2, FR3 and FR4 regions which are human framework regions selected to provide a scaffold conducive for non-human CDR3 amino acid sequences are obtainable by:
 (i) providing
 (a) a collection of sequences of naturally occurring human antibodies each comprising a set of human FR1, FR2, FR3 and FR4 regions; and
 (b) a collection of sequences of naturally occurring non-human antibodies each comprising a set of non-human FR1, FR2, FR3 and FR4 regions, and
 (ii) identifying a plurality of sets of human FR1, FR2, FR3 and FR4 regions which provide a scaffold conducive for non-human CDR3 amino acid sequences by
  determining the parameters framework homology, CDR cosmology, CDR lengths, CDR canonical structure, and adoption of comfortable heavy or light mount angles, and
  selecting sets of human FR1, FR2, FR3 and FR4 regions which exhibit high scores for the parameters,
 and/or
 the two C-terminal amino acids of heavy chain FR2 are optionally non-human, and
 the two C-terminal amino acids of heavy chain FR3 are optionally non-human.

In a further embodiment, the present disclosure provides a population of Acceptor Framework proteins, wherein each Acceptor Framework protein comprises a set of framework regions comprising a first human framework region (FR1), a second human framework region (FR2), a third human framework region (FR3), and a fourth human framework region (FR4); wherein the FR1 and FR2 regions are interspaced by a complementarity determining region 1 (CDR1), the FR2 and FR3 regions are interspaced by a complementarity determining region 2 (CDR2), and the FR3 and FR4 regions are linked directly or are interspaced by a stuffer sequence; and wherein the CDR1 and CDR2 amino acid sequences are diversified among the population of Acceptor Framework proteins, wherein each CDR1 or CDR2 amino acid sequence is independently based (i) on a human CDR1 or CDR2, respectively, or (ii) on a non-human CDR1 or CDR2, respectively, wherein at least some of the CDR1 or CDR2 amino acid sequence have been modified to comprise at least one amino acid present in non-human CDR1 or CDR2 amino acid sequences, respectively, in case of human CDR1 or CDR2, respectively, or to comprise at least one amino acid present in human CDR1 or CDR2 amino acid sequences, respectively, in case of non-human CDR1 or CDR2, respectively; and wherein the human FR1, FR2, FR3 and FR4 regions are human framework regions selected to provide a scaffold conducive for non-human CDR3 amino acid sequences, with the proviso:

that the two C-terminal amino acids of FR2 are optionally non-human, and that the two C-terminal amino acids of FR3 are optionally non-human.

It is understood that the preferred embodiments for the methods of the disclosure and populations of the disclosure also apply to the populations of Acceptor Framework proteins described herein.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. In some embodiments, the FR1 and FR4 regions are human FR1 and FR4 regions. Preferably, also the FR3 and FR4 region is human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

The CDR1 and CDR2 amino acid sequences are diversified among the population of Acceptor Framework proteins, wherein each CDR1 or CDR2 amino acid sequence is independently based i) on a human CDR1 or CDR2, respectively, or ii) on a non-human CDR1 or CDR2, respectively, wherein at least some of the CDR1 or CDR2 amino acid sequences have been modified to contain at least one amino acid present in non-human CDR1 or CDR2 amino acid sequences, respectively, in case of human CDR1 or CDR2, respectively, or to contain at least one amino acid present in human CDR1 or CDR2 amino acid sequences, respectively, in case of non-human CDR1 or CDR2, respectively.

Diversified CDR1 and CDR2 sequences according to the disclosure can be obtained by computationally integrating a plurality, such as $10^4$, $10^5$, or $10^6$-$10^7$ of simulated humanizations across the non-human antibody repertoire and the human acceptor antibody repertoire, in order to generate a mathematically optimal Bayesian representation of the humanization space between non-human and human, converting the probabilistic model to a frequentist interpretation, thereby obtaining a population or library. Each position ends up containing a probability of encountering the human germline residue, the non-human germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment, the human or non-human CDR1 regions and the human and non-human CDR2 regions, on which the diversified CDR1 and CDR2 amino acid sequences are based, are selected from human germline CDR1 regions, human germline CDR2 regions, non-human germline CDR1 regions, non-human germline CDR2 regions, human somatic hypermutation CDR1 regions, human somatic hypermutation CDR2 regions, non-human somatic hypermutation CDR1 regions, non-human somatic hypermutation CDR2 regions, non-human gene conversion CDR1 regions, and non-human gene conversion CDR2 regions.

In a yet further preferred embodiment, the diversified CDR1 and CDR2 amino acid sequences are CDR-H1, CDR-H2, CDR-L1 and/or CDR-L2 sequences.

In a preferred embodiment, the population of Acceptor Framework proteins includes at least one human CDR-H1, and/or a human CDR-H2, and/or a human CDR-L1 and/or a human CDR-L2 sequence.

In a further preferred embodiment, the population of Acceptor Framework proteins includes at least one non-human CDR-H1, and/or a non-human CDR-H2, and/or a non-human CDR-L1 and/or a non-human CDR-L2 sequence.

In some embodiments, the human FR1, FR2, FR3 and FR4 regions are human framework regions selected to provide a scaffold conducive for non-human CDR3 amino acid sequences, with the proviso that the two C-terminal amino acids of FR2 are optionally non-human, and that the two C-terminal amino acids of FR3 are optionally non-human. In one preferred embodiment, a population of the disclosure comprises at least one protein comprising a human FR1, a human FR2, a human FR3 and a human FR4 region, and a human CDR1, and a human CDR2 region.

In another preferred embodiment, a population of the disclosure comprises at least one protein comprising a human FR1, a human FR2, a human FR3 and a human FR4 region, and a non-human CDR1, and a non-human CDR2 region.

In yet another preferred embodiment, the population of the disclosure does not contain a protein comprising a human FR1, a human FR2, a human FR3 and a human FR4 region, and a human CDR1, and a human CDR2 region.

In yet another preferred embodiment, a population of the disclosure does not contain a protein comprising a human FR1, a human FR2, a human FR3 and a human FR4 region, and a non-human CDR1, and a non-human CDR2 region.

A suitable scaffold conducive for non-human CDR3 amino acid sequences is obtainable by selecting a framework set by performing the following steps:

computational imputation of germline repertoire element centroids which are most utilized in functional non-human antibodies generating an amino acid alignment of human frameworks compared to said computationally imputed non-human frameworks and selecting the closest representatives, respectively, that have the same length of CDR-H1, CDR-H2, CDR-L1, and CDR-L2 and similar sequence composition, respectively, further reducing the number of candidates framework sequences by preferring templates that are known to be stable in the art and optionally have worked as previous drugs, further reducing the number of framework candidates by structurally modeling antibodies from non-human and human using these frameworks and analyzing their structural superposition tolerance by root mean squared deviation (RMSD), and selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

Moreover, the two C-terminal amino acids of heavy chain FR2 are optionally non-human, and the two C-terminal amino acids of heavy chain FR3 are optionally non-human, for example in case an SDR is grafted into a scaffold, or in case amino acids surrounding FR2 are substituted, as described above.

In a yet further preferred embodiment, the human FR1, FR2, FR3 and FR4 regions which are human framework regions selected to provide a scaffold conducive for non-human CDR3 amino acid sequences are obtainable by:

(i) providing (a) a collection of sequences of naturally occurring human antibodies each comprising a set of human FR1, FR2, FR3 and FR4 regions; and (b) a collection of sequences of naturally occurring non-human antibodies each comprising a set of non-human FR1, FR2, FR3 and FR4 regions, and (ii) identifying a plurality of sets of human FR1, FR2, FR3 and FR4 regions which provide a scaffold conducive for non-human CDR3 amino acid sequences by determining the parameters framework homology, CDR cosmology, CDR lengths, CDR canonical structure, and adoption of comfortable heavy or light mount angles, and selecting sets of human FR1, FR2, FR3 and FR4 regions which exhibit high scores for the parameters, and/or the two C-terminal amino acids of heavy chain FR2 are optionally non-human, and the two C-terminal amino acids of heavy chain FR3 are optionally non-human.

In a further embodiment, the present disclosure provides the use of a population of nucleic acids of the disclosure, or a population of proteins of the disclosure, for screening for proteins comprising at least one immunoglobulin variable domain, in particular antibodies or fragments thereof, which specifically bind to an antigen of interest. Preferably, the fragment of an antibody comprises at least one immunoglobulin variable domain, in a more preferred embodiment, the fragment of an antibody is a Fv, scFv or Fab.

Methods for screening via display methods are described in detail above.

A protein comprising at least one immunoglobulin variable domain, in particular an antibody or fragment thereof, is understood to specifically bind to an antigen when the protein binds to the antigen, preferably binding with an affinity of Kd of $10^{-6}$, $10^{-7}$, $10^{-8}$, $10^{-9}$ or less, and substantially does not bind to other polypeptides or binds to other polypeptides with at least 10-fold or at least 100-fold weaker affinity, preferably with a Kd of $10^{-6}$, $10^{-5}$, or more.

The strength, or affinity of immunological binding interactions can be expressed in terms of the dissociation constant (Kd) of the interaction, wherein a smaller Kd represents a greater affinity. The Kd value can be determined by methods known in the art, such as at 25° C. by surface plasmon resonance spectroscopy. Systems for performing such analyses are commercially available (e.g. using a Biacore3000™ surface plasmon resonance (SPR) system, Biacore, INC, Piscataway N.J.). Kinetic association rates (kon) and dissociation rates (koff) can be obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant (KD) values can be calculated as koff/kon. Binding affinity of an antibody is generally measured at 25° C., but can also be measured at 37° C.

In some embodiments of any of the various the methods and uses described herein, screening is performed by display of at least one protein on a virus, a cell, or a surface.

In any of the various methods described herein in which it may be advantageously employed, a method may comprise extraction of nucleic acid from a sample. Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent with or without the use of an automated nucleic acid extractor, e.g., the Model 341 DNA Extractor available from Applied Biosystems (Foster City, Calif.); (2) stationary phase adsorption methods; and (3) salt-induced nucleic acid precipitation methods, such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads. In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical.

The extracted polynucleotides from the samples can be sequenced to generate sequencing reads. A variety of suitable sequencing technologies are available. Exemplary sequencing techniques can include, for example emulsion PCR (pyrosequencing from Roche 454, semiconductor sequencing from Ion Torrent, SOLiD sequencing by ligation from Life Technologies, sequencing by synthesis from Intelligent Biosystems), bridge amplification on a flow cell (e.g. Solexa/Illumina), isothermal amplification by Wildfire technology (Life Technologies) or rolonies/nanoballs generated by rolling circle amplification (Complete Genomics, Intelligent Biosystems, Polonator). Sequencing technologies like Heliscope (Helicos), SMRT technology (Pacific Biosciences) or nanopore sequencing (Oxford Nanopore) allow direct sequencing of single molecules without prior clonal amplification may be suitable sequencing platforms. Polynucleotides from a sample may be amplified by any suitable means prior to and/or during sequencing.

In any of the various methods described herein in which it may be advantageously employed, a method may comprise a polynucleotide amplification reaction. In general, "polynucleotide amplification" refers to a process by which one or more copies of a polynucleotide are generated. A variety of suitable amplification processes are available. Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. No. 5,527,670, U.S. Pat. No. 6,033,850, U.S. Pat. No. 5,939,291, and U.S. Pat. No. 6,333,157), and application of an electromagnetic field in combination with primers bound to a magnetically-responsive material (e.g. U.S. Pat. No. 5,545,540). In a variation called RT-PCR, reverse transcriptase (RT) is used to make a complementary DNA (cDNA) from RNA, and the cDNA is then amplified by PCR to produce multiple copies of DNA (e.g. U.S. Pat. No. 5,322,770 and U.S. Pat. No. 5,310,652). Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278). In some cases, isothermal amplification utilizes transcription by an RNA polymerase from a promoter sequence, such as may be incorporated into an oligonucleotide primer. Transcription-based amplification methods commonly used in the art include nucleic acid sequence based amplification, also referred to as NASBA (e.g. U.S. Pat. No. 5,130,238); methods which rely on the use of an RNA replicase to amplify the probe molecule itself, commonly referred to as Qβ replicase (e.g., Lizardi, P. et al. (1988) BioTechnol. 6, 1197-1202); self-sustained sequence replication (e.g., Guatelli, J. et al. (1990) Proc. Natl. Acad. Sci. USA 87, 1874-1878; Landgren (1993) Trends in Genetics 9, 199-202; and HELEN H. LEE et al., NUCLEIC ACID AMPLIFICATION TECHNOLOGIES (1997)); and methods for generating additional transcription templates (e.g. U.S. Pat. No. 5,480,784 and U.S. Pat. No. 5,399,491). Isothermal amplification processes can be linear or exponential.

In one aspect, the disclosure provides systems for performing any of the methods described herein. For example, the system may comprise one or more computer processors programmed to perform one or more steps of a method described herein. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to perform one or more steps of a method in response to a user request. The computer may receive the user request directly (e.g. by way of an input device such as a keyboard, mouse, or touch screen operated by the customer or a user entering a customer request) or indirectly (e.g. through a wired or wireless connection, including over the internet).

In one aspect, the disclosure provides a computer-readable medium comprising codes that, upon execution by one or more processors, implements a method according to any of the methods disclosed herein. Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

In one aspect, the present disclosure provides for use of a composition in the preparation for a medicament for the treatment of a disease or condition of a subject. The compositions may comprise one or more proteins or nucleic acids disclosed herein. In another aspect, the disclosure provides methods of treating a subject for a disease or condition, comprising administering to a subject one or more proteins or nucleic acids disclosed herein, or compositions thereof. The compositions may further comprise one or more pharmaceutically acceptable salts, excipients or vehicles. Compositions may be suitable for various routes of administration, including, but not limited to, parenteral, intraarticular, subcutaneous, intravenous, intramuscular, intraperitoneal, intracerebral, intracerebroventricular, intramuscular, intraocular, intraarterial, or intralesional administration. The disease or condition, by way of non-limiting example, may be selected from the group consisting of an autoimmune disease, a cancer, a metabolic disorder, a cardiovascular condition, a neurological condition, a neuromuscular condition, and an infection. In some embodiments, the therapeutic composition comprises one or more antibodies humanized in accordance with a method of the present disclosure. The specific disease or condition may depend on the therapeutic target, such as the target to which the antibody is directed.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: The Generation of Humanized Antibodies

The generation of humanized antibodies can performed by the following steps:

(a) Immunization of a non-human species.

(b) Lymphocyte preparation from different organs (e.g. spleen, bone marrow, or blood).

(c) RNA isolation from lymphocytes.

(d) Separate PCRs of non-human VH and VL variable regions.

(e) Separate nested PCRs of non-human VH and VL CDR3.

(f) Cloning of VH and/or VL CDR3s into acceptor framework libraries to generate humanized VH and VL fragments.

(g) Cloning of obtained humanized heavy chain, humanized light chains, or humanized scFv into a phage display vector.

(h) Selection for specificity on antigen.

(i) Characterization of individual antibodies.

(j) Optimization based on characterization of successful antibodies and less successful antibodies.

In order to generate the appropriate Acceptor Frameworks, the non-human V-gene scaffolds are compared to their human counterparts to identify human V-genes that are (1) similar at the amino acid level, defined by percent identity by amino acid alignment or similarity as defined by the BLOSUM62 similarity matrix, or some other preferred similarity matrix; (2) optionally possess the same length CDR1 and CDR2 sequences or most similar length CDR1 and CDR2 sequences as the non-human V-gene; (3) have similar canonical classifications of their CDR1 and CDR2 structures (e.g. as determined by crystal structure or as predicted by amino acid motif as determined by non-limiting, exemplary methods set forth in Al-Lazikani, B. et al. Standard conformations for the canonical structures of immunoglobulins. Journal of Molecular Biology 273, 927-948 (1997)); and (4) are observed by crystal structure or predicted by computational modeling to adopt a similar H/L interface mount angle as determined by predicted or observed crystal structures showing the degree shift of the central axis of the light chain Fv compared to a fixed superposition of heavy chain Fv as described earlier. The number of potential humanization frameworks can be further reduced to preferentially choose frameworks that have been previously used in human therapeutics and are known to be stable (e.g. IGHV3 and IGHV1 families of the heavy chain V-gene). The subset of human frameworks that fit these criteria is referred to in this example as "preferred acceptor scaffolds."

A map is generated between every observed antibody in the non-human species and every preferred acceptor scaffold in humans. All sequences from both species are analyzed to: (1) obtain an optionally non-redundant database of amino acid sequences from both species from at least the memory B cell repertoire (2) generate a positional weight matrix (PWM) of amino acid positional variability in the CDR1 and CDR2 of the non-human species and the human species by calculating the relative frequency of amino acids at each position of a specific non-human V-gene and each member of the subset of preferred acceptor scaffolds from humans; (3) blend each of two PWMs from the non-human V-gene and a V-gene from the human preferred acceptor scaffolds to produce a hybrid PWM that contained the amino acid variation observed from both species at each position; (4) optionally adjust the blended PWM to remove cysteine, methionine, and tryptophan residues in order to generate superior therapeutics; and (5) optionally adjust the composition of the blended PWM to bias the library more towards either the human or non-human molecules, as well as to adjust the effective diversity of the library.

The PWMs can be converted to instructions to produce a library of nucleic acid molecules encoding immunoglobulin molecules. Nucleic acid synthesis instructions are generated such that each amino acid is encoded at a position at approximately its frequency within the PWM, with the frequency of each amino acid position independent of the others.

The in silico nucleic acid library produced by these methods can be analyzed by probabilistic simulation to analyze the predicted properties of the synthesized library. The expected frequency of every molecule in the library can be calculated. Mathematical simulation can be used to explore the theoretical humanization of non-human antibodies to evaluate the proximity of the closest humanizations, and the blended PWM can be adjusted to bias the libraries towards a given level of humanization. This is accomplished by iterative Monte Carlo sampling or other methods.

The methods can be used to ensure that for any given epitope of 5-25 amino acids, the library will highly preferentially explore solutions no more than 21 amino acids away from the non-human repertoire and no more than 2 amino acids away from the human repertoire for the epitope in question.

The PWM can then be converted into synthesis instructions to produce a synthetic library, where each position in the CDRs1 and CDR2 contain the diversity observed in the blended library, and the frameworks are human.

The library can be assembled taking CDR-H3s and optimally CDR-L3s from a non-human species post-immunization or post-immune mediated events and transferred into the library by restriction, Gibson overlap extension, PCR overlap extension, or other technologies.

The humanized immunoglobulins can be characterized by their binding affinity to the antigen and proteins with high amino acid similarity to the antigen, such as the homologous protein in a related species. The humanized antibodies can be characterized to identify those that lack binding affinity for off-target molecules. The human antibodies can be characterized to determine their stability and aggregation kinetics/thermodynamics. The population of nucleic acids encoding the antibodies having the desired characteristics can be sequenced, and amino acid residues that are present at higher frequencies in less successful antibodies (e.g.

antibodies with binding affinity below a desired level of affinity, such as an affinity level described herein) or amino acid residues that are present at higher frequencies in more successful antibodies (e.g. antibodies with binding affinity above a desired threshold, such as an affinity level described herein) can be determined. Step (j) of antibody optimization can be accomplished by using the characteristics of unsuccessful and successful antibodies to synthesize novel antibodies that lack particular amino sequence associated with less successful antibodies and possess particular amino acid sequence associated with more successful antibodies, thereby optimizing antibodies.

Example 2: Determination of Appropriate Receptor Frameworks for Murine Antibodies and Characterization of their Frequencies Germline V gene segments from mice can be compared to germline V gene segments from humans to identify preferred acceptor frameworks. Multiple germline mouse V gene segments can be mapped onto individual germline human V gene segments, thereby funneling much of the mouse immunoglobulin repertoire towards particular preferred acceptor frameworks.

Figure 3:
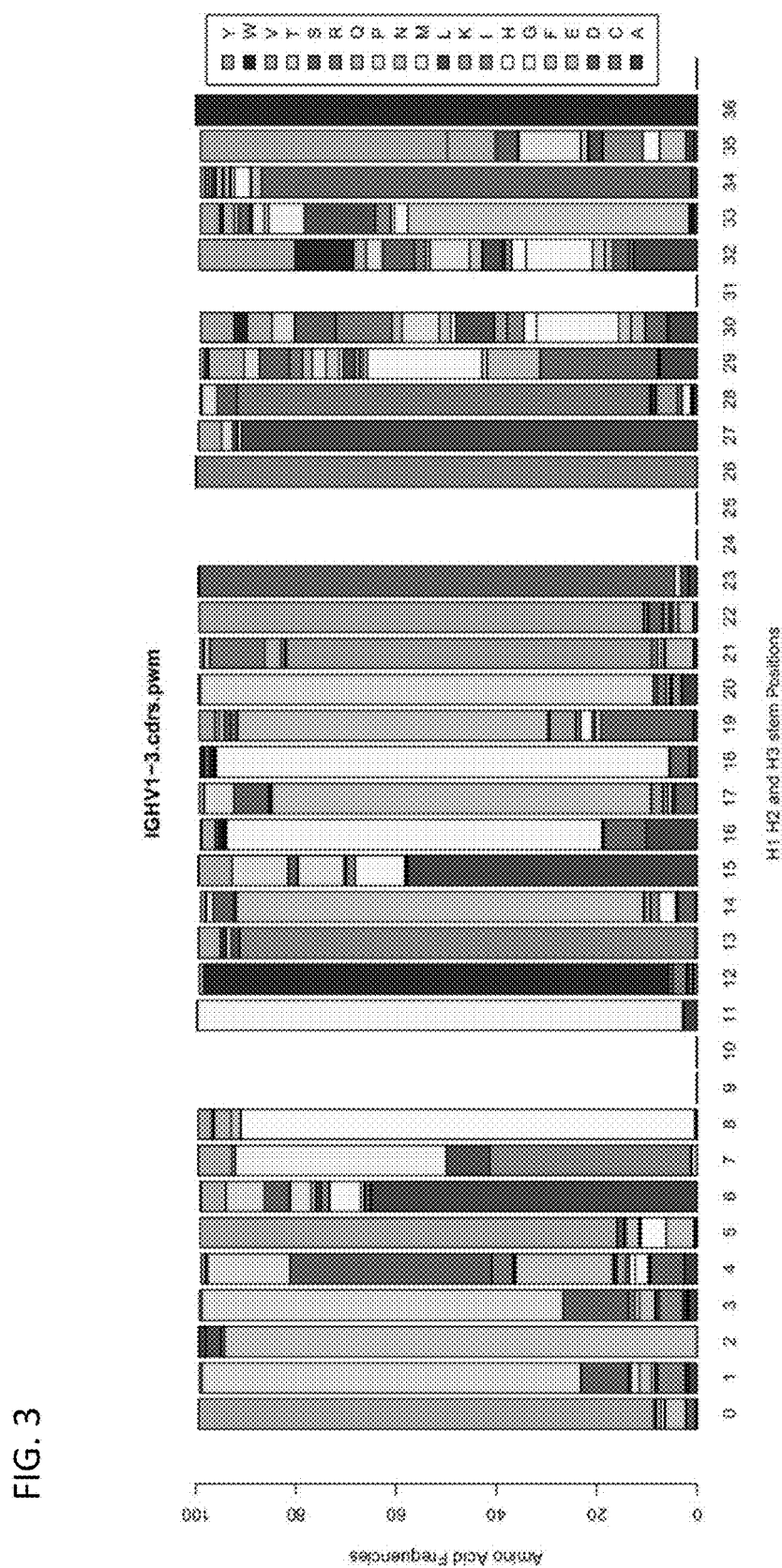
FIG. 3 shows exemplary positional weight matrices (PWM) for human light chain V segment IGHV1-3 CDRS.

RNA from murine lymphocytes can be isolated and the sequences of the immunoglobulins genes determined. The frequencies of the different light-chain immunoglobulin and heavy-chain immunoglobulin V gene segments that map to each human germline V gene segment can be determined. For example, multiple mouse V gene segments that map onto the human acceptor V gene segment IGHV1-3 can be found in the sequences assayed. An exemplary PWM for human immunoglobulin IGHV1-3 CDR sequences is illustrated in FIG. 3.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of producing a population of nucleic acids encoding immunoglobulin variable domains of humanized antibodies, wherein each of the nucleic acids comprises a non-human complementarity determining region 3 (CDR3) encoding sequence embedded in a scaffold-encoding nucleic acid comprising a first human framework the region (FR1) encoding sequence, a second human framework region (FR2) encoding sequence, a third human framework region (FR3) encoding sequence, a fourth human framework region (FR4) encoding sequence, a complementarity determining region 1 (CDR1) encoding sequence, and a complementarity determining region 2 (CDR2) encoding sequence, such that the FR1 encoding sequence and FR2 encoding sequence are interspaced by the CDR1 encoding sequence, the FR2 encoding sequence and FR3 encoding sequence are interspaced by the CDR2 encoding sequence, and the FR3 encoding sequence and FR4 encoding sequence are interspaced by the non-human CDR3 encoding sequence, the method comprising the following steps:
   a) providing at least one non-human CDR3 encoding sequence;
   b) generating, on a computer, a first positional weight matrix (PWM) of amino acid positional variability from naturally-occurring, non-human CDR1s or CDR2s by calculating a first relative frequency of each amino acid at each position of the naturally-occurring, non-human CDR1s or CDR2s;
   c) generating, on the computer, a second PWM of amino acid positional variability from naturally-occurring, human CDR1s or CDR2s by calculating a second relative frequency of amino acids at each position of the naturally-occurring, human CDR1s or CDR2s;
   d) blending, on a computer, the first PWM and the second PWM to produce a blended PWM that provides for amino acid variation observed in both human and non-human CDR1s or CDR2s;
   e) using the blended PWM, generating a plurality of scaffold-encoding nucleic acids comprising different CDR1 encoding sequences or different CDR2 encoding sequences, wherein amino acids of the CDR1 encoding sequences or CDR2 encoding sequences, respectively, occur at about their frequencies at their respective positions within the blended PWM; and
   (f) inserting the non-human CDR3 encoding sequence into the scaffold-encoding nucleic acids, thereby generating the population of encoding humanized antibodies.

2. The method of claim 1, further comprising producing a population of polypeptides from the population of nucleic acids.

3. The method of claim 1, wherein at least 3 nucleic acids of the population of nucleic acids exhibit different CDR1 encoding and/or CDR2 encoding sequences.

4. The method of claim 1, wherein the CDR1 or CDR2 encoding sequences exhibit at least 30% sequence identity to a human CDR1 or human CDR2 encoding sequence, respectively.

5. The method of claim 1, further comprising modifying the CDR1 encoding sequences or CDR2 encoding sequences to increase the immunoglobulin variable domains' similarity to that of the CDR3's native immunoglobulin variable domain with respect to a feature selected from amino acid sequence, cosmology, length, canonical structure, heavy/light interface mount angle, and combinations thereof.

6. The method of claim 1, comprising adjusting the blended PWM to remove a cysteine, methionine or tryptophan.

7. The method of claim 1, comprising adjusting the blended PWM towards the amino acid positional variability of the human CDR's or CDR2s or towards the amino acid positional variability of the non-human CDR's or CDR2s.

8. The method of claim 1 wherein the humanized antibodies are selected from scFv, Fv, Fab, Fab' and F(ab')2.

9. The method of claim 1, wherein at least two of the nucleic acids of the population of nucleic acids encode different CDR3 amino acid sequences.

10. The method of claim 1, wherein at least 10 or more nucleic acids of the population exhibit different CDR1 encoding sequences or different CDR2 encoding sequences.

11. The method of claim 1, comprising
   a) generating, on a computer, the first PWM of amino acid positional variability from naturally-occurring, non-human CDR1s and CDR2s by calculating the first relative frequency of each amino acid at each position of the naturally-occurring, non-human CDR's and CDR2s;
   b) generating, on the computer, the second PWM of amino acid positional variability from naturally-occurring, human CDR's or CDR2s by calculating the second relative frequency of amino acids at each position of the naturally-occurring, human CDR's or CDR2s;
   c) blending, on the computer, the first PWM and the second PWM to produce the blended PWM that provides for amino acid variation observed in both human and non-human CDR's and CDR2s;
   d) using the blended PWM, generating the plurality of scaffold-encoding nucleic acids comprising different CDR1 encoding sequences and different CDR2 encoding sequences, wherein amino acids of the CDR1 encoding sequences and CDR2 encoding sequences, respectively, occur at about their frequencies at their respective positions within the blended PWM.

* * * * *

```
                         SEQUENCE LISTING

<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(13)
<223> OTHER INFORMATION: Any amino acid

<400> SEQUENCE: 1

Cys Ala Arg Xaa Xaa Xaa Xaa Xaa Xaa Xaa Xaa Xaa Xaa Asp Tyr Trp
1               5                   10                  15

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(18)
<223> OTHER INFORMATION: Any amino acid

<400> SEQUENCE: 2

Gly Leu Glu Trp Val Ser Xaa Xaa Xaa Xaa Xaa Xaa Xaa Xaa Xaa Xaa
1               5                   10                  15

Xaa Xaa Asp Ser Val Lys Gly Arg Phe Thr
            20                  25
```